US006771993B2

(12) United States Patent
Rule et al.

(10) Patent No.: US 6,771,993 B2
(45) Date of Patent: Aug. 3, 2004

(54) SAMPLE ADAPTER

(75) Inventors: Peter Rule, Los Altos Hills, CA (US); James R. Braig, Piedmont, CA (US); Philip C. Hartstein, Cupertino, CA (US); Jennifer H. Gable, Walnut Creek, CA (US)

(73) Assignee: OptiScan Biomedical Corporation, Alameda, CA (US)

( * ) Notice: Subject to any disclaimer, the term of this patent is extended or adjusted under 35 U.S.C. 154(b) by 0 days.

(21) Appl. No.: 10/219,996

(22) Filed: Aug. 15, 2002

(65) Prior Publication Data

US 2003/0060694 A1 Mar. 27, 2003

Related U.S. Application Data

(63) Continuation-in-part of application No. 10/015,932, filed on Nov. 2, 2001.
(60) Provisional application No. 60/313,082, filed on Aug. 16, 2001.

(51) Int. Cl.[7] .................................................. A61B 5/00
(52) U.S. Cl. ......................... 600/316; 600/322; 600/365
(58) Field of Search ................................. 600/309–310, 600/316, 322, 323, 331, 365

(56) References Cited

U.S. PATENT DOCUMENTS

| | | |
|---|---|---|
| 4,305,659 A | 12/1981 | Bilstad et al. |
| 4,350,441 A | 9/1982 | Wicnienski |
| 4,397,956 A | 8/1983 | Maggio |
| 4,407,290 A | 10/1983 | Wilber |
| 4,655,225 A | 4/1987 | Dahne et al. |
| 4,704,029 A | 11/1987 | Van Heuvelen |
| 4,873,993 A | 10/1989 | Meserol et al. |
| 4,882,492 A | 11/1989 | Schlager |
| 4,968,137 A | 11/1990 | Yount |
| 4,990,772 A | 2/1991 | Rosenthal |
| 5,028,787 A | 7/1991 | Rosenthal et al. |
| 5,059,394 A | 10/1991 | Phillips et al. |
| 5,068,536 A | 11/1991 | Rosenthal |

(List continued on next page.)

OTHER PUBLICATIONS

Rickheim et al., *Type 2 Diabetes Basics*International Diabetes Center, Institute for Research and Education, 2000, p. 16.
Jungheim and Koschinsky, *Risky Delay of Hypoglycemia Detection by Glucose Monitoring at the Arm*, Diabetes Care vol. 24, No. 7, pp. 1303–1304, Jul. 2001.
McGarraugh, *Response to Jungheim and Koschinsky*, Diabetes Care vol. 24, No. 7, pp. 1304–1306, Jul. 2001.
Excerpt (pp. 1–7, 13–20, 23–27) of U.S. Department of Health and Human Services, Food and Drug Administration, Center for Devices and Radiological Health, *Meeting of the Clinical Chemistry and Clinical Toxicology Devices Panel of the Medical Devices Advisory Committee*, Oct. 29, 2001.
McGarraugh et al., *Glucose Measurements Using Blood Extracted from the Forearm and the Finger*, TheraSense, Inc., 2001.
Ellison et al., *Rapid Changes in Postprandial Blood Glucose Produce Concentration Differences at Finger, Forearm, and Thigh Sampling Sites*, Diabetes Care vol. 25, No. 6, pp. 961–964, Jun. 2002.

*Primary Examiner*—Mary Beth Jones
*Assistant Examiner*—Matthew Kremer
(74) *Attorney, Agent, or Firm*—Knobbe Martens Olson & Bear LLP

(57) ABSTRACT

An adapter presents a sample of bodily fluid, such as whole blood, including an analyte to an analyzer window of a non-invasive monitor. The adapter comprises a base material that comprises a first side and a second side. The adapter also comprises a sample accommodating volume extending between an opening in the second side of the base material and an opening in the first side of the base material.

10 Claims, 25 Drawing Sheets

U.S. PATENT DOCUMENTS

| | | | |
|---|---|---|---|
| 5,133,451 A | * 7/1992 | Boyd et al. ............... 206/81 |
| 5,140,985 A | 8/1992 | Schroeder et al. |
| 5,166,517 A | * 11/1992 | Volgyesi ............... 250/252.1 |
| 5,179,005 A | 1/1993 | Phillips et al. |
| 5,204,525 A | 4/1993 | Hillman et al. |
| 5,204,532 A | 4/1993 | Rosenthal |
| 5,249,584 A | 10/1993 | Karkar et al. |
| 5,278,627 A | 1/1994 | Aoyagi et al. |
| 5,286,454 A | 2/1994 | Nilsson et al. |
| 5,371,020 A | 12/1994 | Frischauf |
| 5,377,674 A | 1/1995 | Kuestner |
| 5,430,542 A | 7/1995 | Shepherd |
| 5,507,288 A | * 4/1996 | Bocker et al. ............... 600/322 |
| 5,515,847 A | 5/1996 | Braig et al. |
| 5,576,544 A | 11/1996 | Rosenthal |
| 5,615,672 A | 4/1997 | Braig et al. |
| 5,666,956 A | 9/1997 | Buchert |
| 5,674,457 A | 10/1997 | Williamsson et al. |
| 5,773,301 A | 6/1998 | Ziegler |
| 5,792,049 A | 8/1998 | Eppstein et al. |
| 5,815,258 A | 9/1998 | Nakanishi |
| 5,817,008 A | * 10/1998 | Rafert et al. ............... 600/323 |
| 5,844,686 A | 12/1998 | Treptow et al. |
| 5,891,025 A | 4/1999 | Buschmann et al. |
| 5,900,632 A | 5/1999 | Sterling et al. |
| 5,902,246 A | 5/1999 | McHenry et al. |
| 5,944,660 A | 8/1999 | Kimball et al. |
| 5,977,545 A | 11/1999 | Haar et al. |
| 6,002,482 A | 12/1999 | Rothfritz et al. |
| 6,018,673 A | * 1/2000 | Chin et al. ............... 600/322 |
| 6,025,597 A | 2/2000 | Sterling et al. |
| 6,049,081 A | 4/2000 | Sterling et al. |
| 6,066,847 A | 5/2000 | Rosenthal |
| 6,072,180 A | 6/2000 | Kramer et al. |
| 6,084,660 A | 7/2000 | Shartle |
| 6,102,872 A | 8/2000 | Doneen et al. |
| 6,157,041 A | 12/2000 | Thomas et al. |
| 6,161,028 A | 12/2000 | Braig et al. |
| 6,162,639 A | 12/2000 | Douglas |
| 6,196,046 B1 | 3/2001 | Braig et al. |
| 6,197,494 B1 | 3/2001 | Oberhardt |
| 6,198,949 B1 | 3/2001 | Braig et al. |
| 6,261,519 B1 | 7/2001 | Harding et al. |
| 6,285,448 B1 | 9/2001 | Kuenstner |
| 6,312,888 B1 | 11/2001 | Wong et al. |
| 6,636,753 B1 | 10/2003 | Braig et al. |
| 6,678,542 B2 | 1/2004 | Braig et al. |
| 2003/0040683 A1 | 2/2003 | Rule et al. |
| 2003/0175806 A1 | 9/2003 | Rule et al. |

* cited by examiner

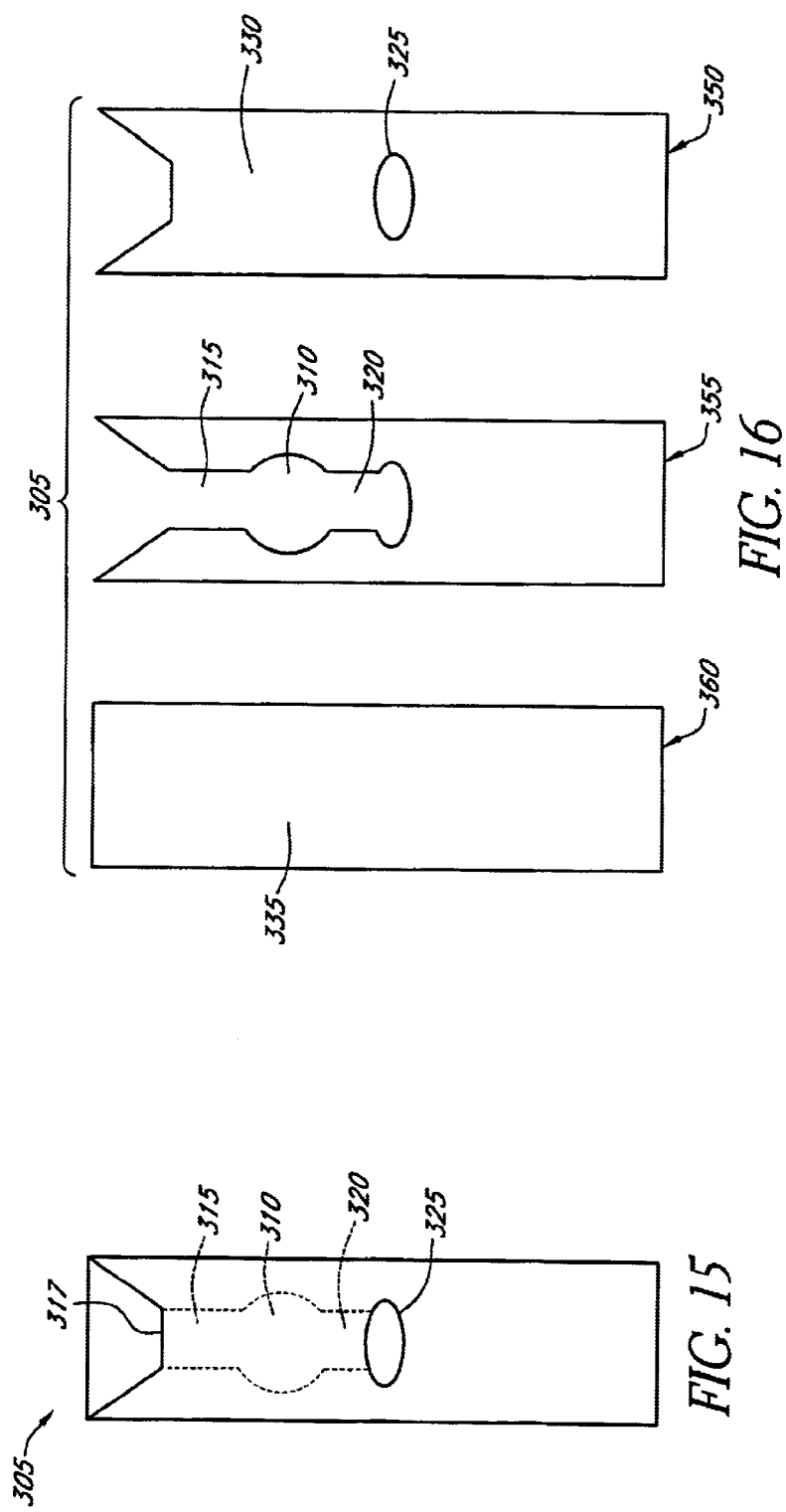

SAMPLE ADAPTER

RELATED APPLICATIONS

This application is a continuation-in-part of U.S. application Ser. No. 10/015,932, filed Nov. 2, 2001, entitled CALIBRATOR, and also claims the benefit of U.S. Provisional Patent Application No. 60/313,082, filed Aug. 16, 2001, entitled ANALYTE MEASUREMENT ERROR CORRECTION METHOD AND DEVICE, the entire contents of both of which are hereby incorporated by reference.

BACKGROUND OF THE INVENTION

1. Field of the Invention

This invention relates generally to determining analyte concentrations within living tissue.

2. Description of the Related Art

Millions of diabetics are forced to draw blood on a daily basis to determine their blood glucose levels. A search for a non-invasive methodology to accurately determine blood glucose levels has been substantially expanded in order to alleviate the discomfort of these individuals.

SUMMARY OF THE INVENTION

A significant advance in the state of the art of non-invasive blood glucose analysis has been realized by an apparatus taught in U.S. Pat. No. 6,198,949, titled SOLID-STATE NON-INVASIVE INFRARED ABSORPTION SPECTROMETER FOR THE GENERATION AND CAPTURE OF THERMAL GRADIENT SPECTRA FROM LIVING TISSUE, issued Mar. 6, 2001; and by methodology taught in U.S. Pat. No. 6,161,028, titled METHOD FOR DETERMINING ANALYTE CONCENTRATION USING PERIODIC TEMPERATURE MODULATION AND PHASE DETECTION, issued Dec. 19, 2000; and in the Assignee's U.S. patent application Ser. No. 09/538,164, titled METHOD AND APPARATUS FOR DETERMINING ANALYTE CONCENTRATION USING PHASE AND MAGNITUDE DETECTION OF A RADIATION TRANSFER FUNCTION. Additional information relating to calibration of such non-invasive blood analysis is taught in U.S. Pat. No. 6,049,081, titled SUBSURFACE THERMAL GRADIENT SPECTROMETRY, issued Apr. 11, 2000; and by U.S. Pat. No. 6,196,046 B1, titled DEVICES AND METHODS FOR CALIBRATION OF A THERMAL GRADIENT SPECTROMETER, issued Mar. 6, 2001. The entire disclosure of all of the above mentioned patents and patent applications are hereby incorporated by reference herein and made a part of this specification.

U.S. Pat. No. 6,198,949 discloses a spectrometer for non-invasive measurement of thermal gradient spectra from living tissue. The spectrometer includes an infrared transmissive thermal mass, referred to as a thermal mass window, for inducing a transient temperature gradient in the tissue by means of conductive heat transfer with the tissue, and a cooling system in operative combination with the thermal mass for the cooling thereof. Also provided is an infrared sensor for detecting infrared emissions from the tissue as the transient temperature gradient progresses into the tissue, and for providing output signals proportional to the detected infrared emissions. A data capture system is provided for sampling the output signals received from the infrared sensor as the transient temperature gradient progresses into the tissue. The transient thermal gradients arising due to the intermittent heating and cooling of the patient's skin generate thermal spectra which yield very good measurements of the patient's blood glucose levels.

Although the apparatus taught in the above-mentioned U.S. Pat. No. 6,198,949 has led to a significant advance in the state of the art of non-invasive blood glucose analysis, one possible source of error in such analysis arises due to physiological variation across the patient population. This variation, as well as other factors, can introduce systematic error into the measurements being performed.

In one embodiment, there is provided an adapter for presenting a sample of body fluid including an analyte to a window of a noninvasive analyte detection system. The adapter comprises a base material comprising a first side and a second side, and a sample accommodating volume extending between an opening in the second side of the base material and an opening in the first side of the base material.

In another embodiment, there is provided an adapter for presenting a sample of whole blood including an analyte to a window of a noninvasive analyte detection system. The adapter comprises a base material comprising a first side and a second side, and an optically transparent layer comprising a first side and a second side. The second side of the optically transparent layer is positioned proximate the first side of the base material. The adapter further comprises a sample accommodating volume extending between the second side of the optically transparent layer and an opening in the second side of the base material.

In another embodiment, there is provided an adapter for presenting a sample of whole blood including an analyte to a window of a noninvasive analyte detection system. The adapter comprises a base material comprising a first side having a first opening and a second side having a second opening, and a sample accommodating volume formed in the base material and extending between the first opening and the second opening.

In another embodiment, there is provided a method for calibrating a noninvasive detection unit including a window. The method comprises withdrawing a sample of bodily fluid from a patient, positioning the sample over the window, analyzing the sample with the noninvasive detection unit and generating an invasive-measurement output representing the concentration of an analyte. The method further comprises placing the window in contact with the skin of the patient, analyzing the patient's tissue with the noninvasive detection unit and generating a noninvasive-measurement output representing the concentration of the analyte. The method further comprises comparing the invasive-measurement output and the noninvasive-measurement output to estimate an error, and correcting the noninvasive-measurement output based on the error.

In another embodiment, there is provided a method for calibrating a noninvasive detection unit including a window. The method comprises determining whether there is a restricted period in effect, selecting an on-site or an alternative site measurement location based on whether a restricted period is in effect, and withdrawing an sample of bodily fluid from a patient at the selected measurement location, wherein the sample comprises at least one analyte. The method further comprises positioning the sample over the window, analyzing the analyte in the sample using the noninvasive detection unit and generating an invasive-measurement output representing a characteristic of the analyte. The method further comprises placing the window of the noninvasive detection unit in contact with the skin of the patient, analyzing the analyte in the tissue of the patient with the noninvasive detection unit, and generating a noninvasive-measurement output representing the characteristic of the analyte. The method further comprises comparing the invasive-measurement Output and the noninvasive-measurement output to estimate an error, and correcting the noninvasive-measurement output based on the error.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention, certain preferred embodiments and modifications thereof will become apparent to those skilled in the art from the detailed description herein having reference to the figures that follow, of which:

FIG. 15 is a plan view of another embodiment of a cuvette for use less whole-blood detection system.

FIG. 16 is a disassembled plan view of the cuvette shown in FIG. 15.

FIG. 17 is a side view of the cuvette of FIG. 15.

DETAILED DESCRIPTION OF THE PREFERRED EMBODIMENTS

Although certain preferred embodiments and examples are disclosed below, it will be understood by those skilled in the art that the invention extends beyond the specifically disclosed embodiments to other alternative embodiments and/or uses of the invention and obvious modifications and equivalents thereof. Thus, it is intended that the scope of the invention herein disclosed should not be limited by the particular disclosed embodiments described below.

I. Overview of Analyte Detection Systems

Disclosed herein are analyte detection systems, including a noninvasive system discussed largely in part A below and a whole-blood system discussed largely in part B below. Also disclosed are various methods, including methods for detecting the concentration of an analyte in a material sample. The noninvasive system/method and the whole-blood system/method are related in that they both can employ optical measurement. As used herein with reference to measurement apparatus and methods, "optical" is a broad term and is used in its ordinary sense and refers, without limitation, to identification of the presence or concentration of an analyte in a material sample without requiring a chemical reaction to take place. As discussed in more detail below, the two approaches each can operate independently to perform an optical analysis of a material sample. The two approaches can also be combined in an apparatus, or the two approaches can be used together to perform different steps of a method.

In one embodiment, the two approaches are combined to perform calibration of an apparatus, e.g., of an apparatus that employs a noninvasive approach. In another embodiment, an advantageous combination of the two approaches performs an invasive measurement to achieve greater accuracy and a whole-blood measurement to minimize discomfort to the patient. For example, the whole-blood technique may be more accurate than the noninvasive technique at certain times of the day, e.g., at certain times after a meal has been consumed, or after a drug has been administered.

It should be understood, however, that any of the disclosed devices may be operated in accordance with any suitable detection methodology, and that any disclosed method may be employed in the operation of any suitable device. Furthermore, the disclosed devices and methods are applicable in a wide variety of situations or modes of operation, including but not limited to invasive, noninvasive, intermittent or continuous measurement, subcutaneous implantation, wearable detection systems, or any combination thereof.

Any method which is described and illustrated herein is not limited to the exact sequence of acts described, nor is it necessarily limited to the practice of all of the acts set forth. Other sequences of events or acts, or less than all of the events, or simultaneous occurrence of the events, may be utilized in practicing the method(s) in question.

A. Noninvasive System

1. Monitor Structure

Figure 1:
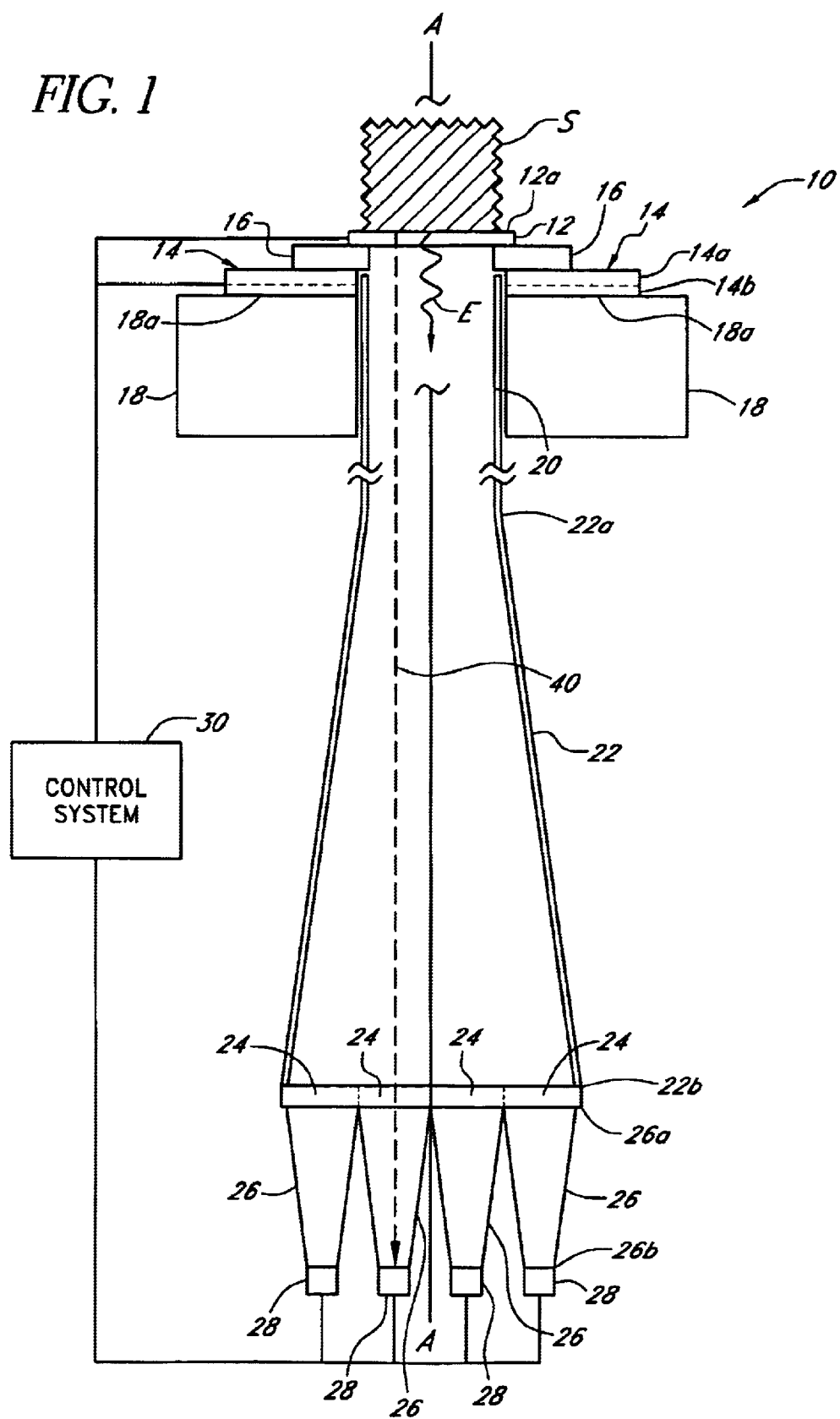
FIG. 1 is a schematic view of a noninvasive optical detection system.

FIG. 1 depicts a noninvasive optical detection system (hereinafter "noninvasive system") 10 in a presently preferred configuration. The depicted noninvasive system 10 is particularly suited for noninvasively detecting the concentration of an analyte in a material sample S, by observing the infrared energy emitted by the sample, as will be discussed in further detail below.

As used herein, the term "noninvasive" is a broad term and is used in its ordinary sense and refers, without limitation, to analyte detection devices and methods which have the capability to determine the concentration of an analyte in in-vivo tissue samples or bodily fluids. It should be understood, however, that the noninvasive system 10 disclosed herein is not limited to noninvasive use, as the noninvasive system 10 may be employed to analyze an in-vitro fluid or tissue sample which has been obtained invasively or noninvasively. As used herein, the term "invasive" is a broad term and is used in its ordinary sense and refers, without limitation, to analyte detection methods which involve the removal of fluid samples through the skin. As used herein, the term "material sample" is a broad term and is used in its ordinary sense and refers, without limitation, to any collection of material which is suitable for analysis by the noninvasive system 10. For example, the material sample S may comprise a tissue sample, such as a human forearm, placed against the noninvasive system 10. The material sample S may also comprise a volume of a bodily fluid, such as whole blood, blood component(s), interstitial fluid or intercellular fluid obtained invasively, or saliva or urine obtained noninvasively, or any collection of organic or inorganic material. As used herein, the term "analyte" is a broad term and is used in its ordinary sense and refers, without limitation, to any chemical species the presence or concentration of which is sought in the material sample S by the noninvasive system 10. For example, the analyte(s) which may be detected by the noninvasive system 10 include but are not limited to glucose, ethanol, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, cytochrome, various proteins and chromophores, microcalcifications, electrolytes, sodium, potassium, chloride, bicarbonate, and hormones. As used herein to describe measurement techniques, the term "continuous" is a broad term and is used in its ordinary sense and refers, without limitation, to the taking of discrete measurements more frequently than about once every 10 minutes, and/or the taking of a stream or series of measurements or other data over any suitable time interval, for example, over an interval of one to several seconds, minutes, hours, days, or longer. As used herein to describe measurement techniques, the term "intermittent" is a broad term and is used in its ordinary sense and refers, without limitation, to the taking of measurements less frequently than about once every 10 minutes.

The noninvasive system 10 preferably comprises a window assembly 12, although in some embodiments the window assembly 12 may be omitted. One function of the window assembly 12 is to permit infrared energy E to enter the noninvasive system 10 from the sample S when it is placed against an upper surface 12a of the window assembly 12. The window assembly 12 includes a heater layer (see discussion below) which is employed to heat the material sample S and stimulate emission of infrared energy therefrom. A cooling system 14, preferably comprising a Peltier-type thermoelectric device, is in thermally conductive relation to the window assembly 12 so that the temperature of the window assembly 12 and the material sample S can be manipulated in accordance with a detection methodology discussed in greater detail below. The cooling system 14 includes a cold surface 14a which is in thermally conductive relation to a cold reservoir 16 and the window assembly 12, and a hot surface 14b which is in thermally conductive relation to a heat sink 18.

As the infrared energy E enters the noninvasive system 10, it first passes through the window assembly 12, then through an optical mixer 20, and then through a collimator 22. The optical mixer 20 preferably comprises a light pipe having highly reflective inner surfaces which randomize the directionality of the infrared energy E as it passes therethrough and reflects against the mixer walls. The collimator 22 also comprises a light pipe having highly-reflective inner walls, but the walls diverge as they extend away from the mixer 20. The divergent walls cause the infrared energy E to tend to straighten as it advances toward the wider end of the collimator 22, due to the angle of incidence of the infrared energy when reflecting against the collimator walls.

From the collimator 22 the infrared energy E passes through an array of filters 24, each of which allows only a selected wavelength or band of wavelengths to pass therethrough. These wavelengths/bands are selected to highlight or isolate the absorptive effects of the analyte of interest in the detection methodology discussed in greater detail below. Each filter 24 is preferably in optical communication with a concentrator 26 and an infrared detector 28. The concentrators 26 have highly reflective, converging inner walls which concentrate the infrared energy as it advances toward the detectors 28, increasing the density of the energy incident upon the detectors 28.

The detectors 28 are in electrical communication with a control system 30 which receives electrical signals from the detectors 28 and computes the concentration of the analyte in the sample S. The control system 30 is also in electrical communication with the window 12 and cooling system 14, so as to monitor the temperature of the window 12 and/or cooling system 14 and control the delivery of electrical power to the window 12 and cooling system 14.

a. Window Assembly

Figure 2:
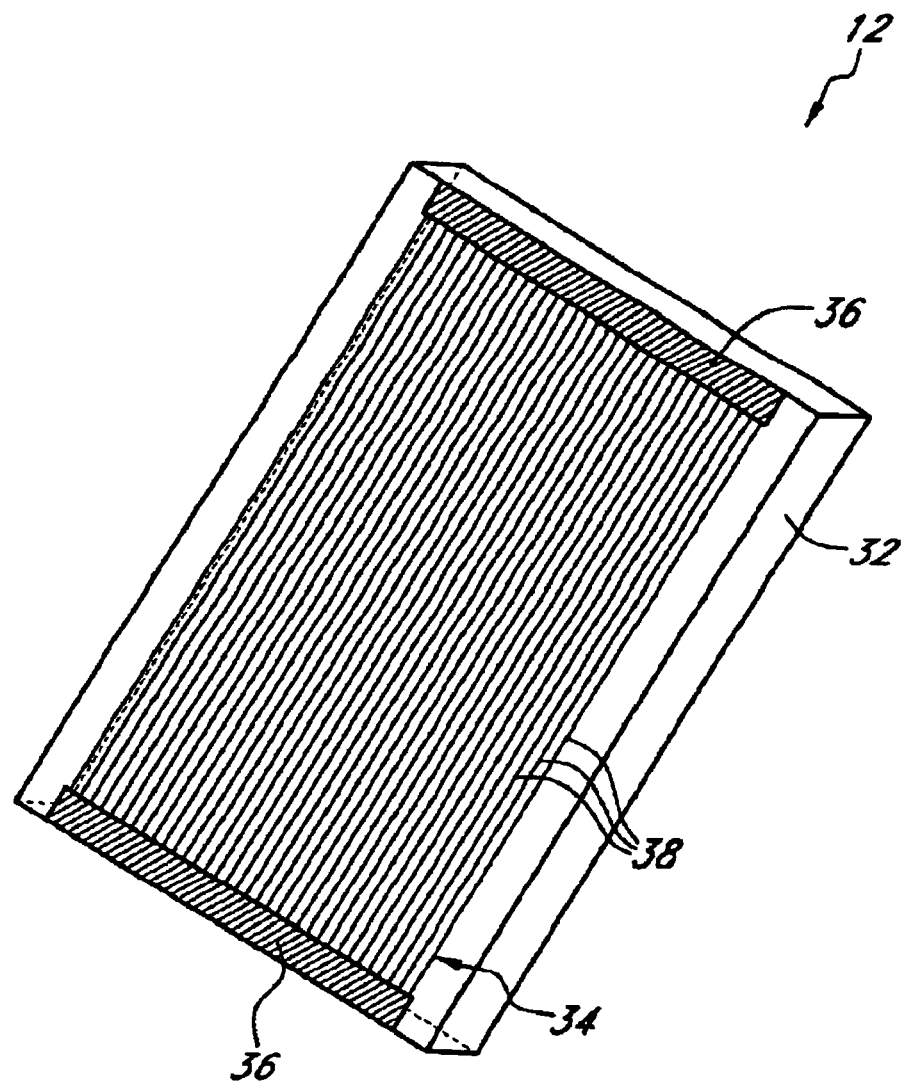
FIG. 2 is a perspective view of a window assembly for use with the noninvasive detection system.

A preferred configuration of the window assembly 12 is shown in perspective, as viewed from its underside (in other words, the side of the window assembly 12 opposite the sample S), in FIG. 2. The window assembly 12 generally comprises a main layer 32 formed of a highly infrared-transmissive material and a heater layer 34 affixed to the underside of the main layer 32. The main layer 32 is preferably formed from diamond, most preferably from chemical-vapor-deposited ("CVD") diamond, with a preferred thickness of about 0.25 millimeters. In other embodiments alternative materials which are highly infrared-transmissive, such as silicon or germanium, may be used in forming the main layer 32.

The heater layer 34 preferably comprises bus bars 36 located at opposing ends of an array of heater elements 38. The bus bars 36 are in electrical communication with the elements 38 so that, upon connection of the bus bars 36 to a suitable electrical power source (not shown) a current may be passed through the elements 38 to generate heat in the window assembly 12. The heater layer 34 may also include one or more temperature sensors (not shown), such as thermistors or resistance temperature devices (RTDs), to measure the temperature of the window assembly 12 and provide temperature feedback to the control system 30 (see FIG. 1).

Still referring to FIG. 2, the heater layer 34 preferably comprises a first adhesion layer of gold or platinum (hereinafter referred to as the "gold" layer) deposited over an alloy layer which is applied to the main layer 32. The alloy layer comprises a material suitable for implementation of the heater layer 34, such as, by way of example, 10/90 titanium/tungsten, titanium/platinum, nickel/chromium, or other similar material. The gold layer preferably has a thickness of about 4000 Å, and the alloy layer preferably has a thickness ranging between about 300 Å and about 500 Å. The gold layer and/or the alloy layer may be deposited onto the main layer 32 by chemical deposition including, but not necessarily limited to, vapor deposition, liquid deposition, plating, laminating, casting, sintering, or other forming or deposition methodologies well known to those or ordinary skill in the art. If desired, the heater layer 34 may be covered with an electrically insulating coating which also enhances adhesion to the main layer 32. One preferred coating material is aluminum oxide. Other acceptable materials include, but are not limited to, titanium dioxide or zinc selenide.

The heater layer 34 may incorporate a variable pitch distance between centerlines of adjacent heater elements 38 to maintain a constant power density, and promote a uniform temperature, across the entire layer 34. Where a constant pitch distance is employed, the preferred distance is at least about 50–100 microns. Although the heater elements 38 generally have a preferred width of about 25 microns, their width may also be varied as needed for the same reasons stated above.

Alternative structures suitable for use as the heater layer 34 include, but are not limited to, thermoelectric heaters, radiofrequency (RF) heaters, infrared radiation heaters, optical heaters, heat exchangers, electrical resistance heating grids, wire bridge heating grids, or laser heaters. Whichever type of heater layer is employed, it is preferred that the heater layer obscures about 10% or less of the window assembly 12.

In a preferred embodiment, the window assembly 12 comprises substantially only the main layer 32 and the heater layer 34. Thus, when installed in an optical detection system such as the noninvasive system 10 shown in FIG. 1, the window assembly 12 will facilitate a minimally obstructed optical path between a (preferably flat) upper surface 12a of the window assembly 12 and the infrared detectors 28 of the noninvasive system 10. The optical path 32 in the preferred noninvasive system 10 proceeds only through the main layer 32 and heater layer 34 of the window assembly 12 (including any antireflective, index-matching, electrical insulating or protective coatings applied thereto or placed therein), through the optical mixer 20 and collimator 22 and to the detectors 28.

Figure 3:
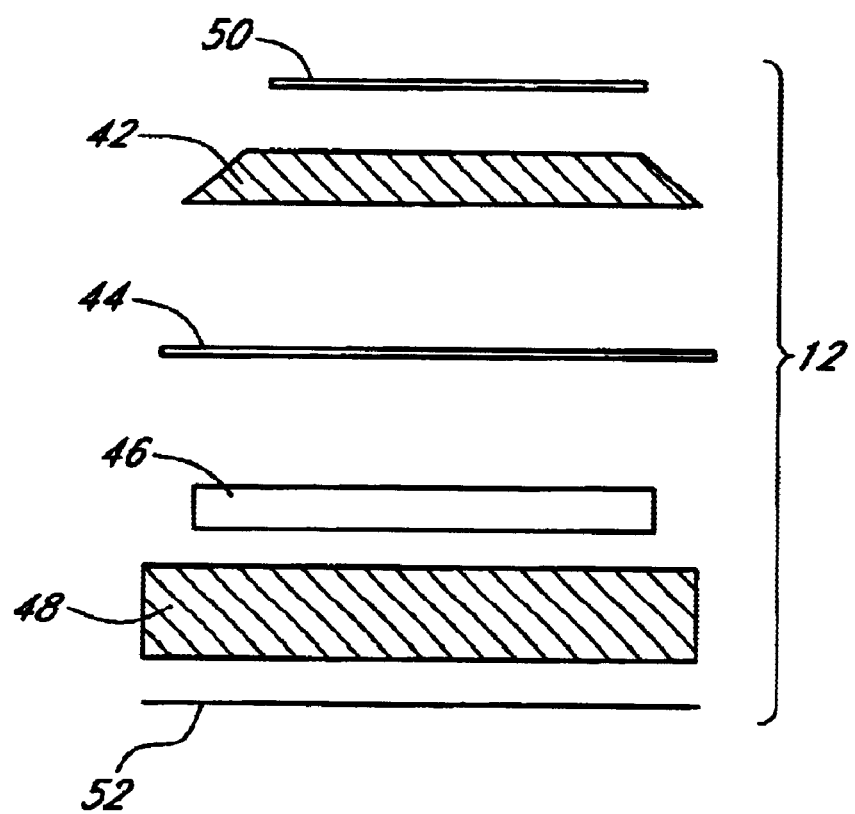
FIG. 3 is an exploded schematic view of an alternative window assembly for use with the noninvasive detection system.

FIG. 3 depicts an exploded side view of an alternative configuration for the window assembly 12, which may be used in place of the configuration shown in FIG. 2. The window assembly 12 depicted in FIG. 3 includes near its upper surface (the surface intended for contact with the sample S) a highly infrared-transmissive, thermally conductive spreader layer 42. Underlying the spreader layer 42 is a heater layer 44. A thin electrically insulating layer (not shown), such as layer of aluminum oxide, titanium dioxide or zinc selenide, may be disposed between the heater layer 44 and the spreader layer 42. (An aluminum oxide layer also increases adhesion of the heater layer 44 to the spreader layer 42.) Adjacent to the heater layer 44 is a thermal insulating and impedance matching layer 46. Adjacent to the thermal insulating layer 46 is a thermally conductive inner layer 48. The spreader layer 42 is coated on its top surface with a thin layer of protective coating 50. The bottom surface of the inner layer 48 is coated with a thin overcoat layer 52. Preferably, the protective coating 50 and the overcoat layer 52 have antireflective properties.

The spreader layer 42 is preferably formed of a highly infrared-transmissive material having a high thermal conductivity sufficient to facilitate heat transfer from the heater layer 44 uniformly into the material sample S when it is placed against the window assembly 12. Other effective materials include, but are not limited to, CVD diamond, diamondlike carbon, gallium arsenide, germanium, and other infrared-transmissive materials having sufficiently high thermal conductivity. Preferred dimensions for the spreader layer 42 are about one inch in diameter and about 0.010 inch thick. As shown in FIG. 3, a preferred embodiment of the spreader layer 42 incorporates a beveled edge. Although not required, an approximate 45-degree bevel is preferred.

The protective layer 50 is intended to protect the top surface of the spreader layer 42 from damage. Ideally, the protective layer is highly infrared-transmissive and highly resistant to mechanical damage, such as scratching or abrasion. It is also preferred that the protective layer 50 and the overcoat layer 52 have high thermal conductivity and anti-reflective and/or index-matching properties. A satisfactory material for use as the protective layer 50 and the overcoat layer 52 is the multi-layer Broad Band Anti-Reflective Coating produced by Deposition Research Laboratories, Inc. of St. Charles, Mo. Diamondlike carbon coatings are also suitable.

Except as noted below, the heater layer 44 is generally similar to the heater layer 34 employed in the window assembly shown in FIG. 2. Alternatively, the heater layer 44 may comprise a doped infrared-transmissive material, such as a doped silicon layer, with regions of higher and lower resistivity. The heater layer 44 preferably has a resistance of about 2 ohms and has a preferred thickness of about 1,500 angstroms. A preferred material for forming the heater layer 44 is a gold alloy, but other acceptable materials include, but are not limited to, platinum, titanium, tungsten, copper, and nickel.

The thermal insulating layer 46 prevents the dissipation of heat from the heater element 44 while allowing the cooling system 14 to effectively cool the material sample S (see FIG. 1). This layer 46 comprises a material having thermally insulative (e.g., lower thermal conductivity than the spreader layer 42) and infrared transmissive qualities. A preferred material is a germanium-arsenic-selenium compound of the calcogenide glass family known as AMTIR-1 produced by Amorphous Materials, Inc. of Garland, Tex. The pictured embodiment has a diameter of about 0.85 inches and a preferred thickness in the range of about 0.005 to about 0.010 inches. As heat generated by the heater layer 44 passes through the spreader layer 42 into the material sample S, the thermal insulating layer 46 insulates this heat.

The inner layer 48 is formed of thermally conductive material, preferably crystalline silicon formed using a conventional floatzone crystal growth method. The purpose of the inner layer 48 is to serve as a cold-conducting mechanical base for the entire layered window assembly.

The overall optical transmission of the window assembly 12 shown in FIG. 3 is preferably at least 70%. The window assembly 12 of FIG. 3 is preferably held together and secured to the noninvasive system 10 by a holding bracket (not shown). The bracket is preferably formed of a glass-filled plastic, for example Ultem 2300, manufactured by General Electric. Ultem 2300 has low thermal conductivity which prevents heat transfer from the layered window assembly 12.

b. Cooling System

The cooling system 14 (see FIG. 1) preferably comprises a Peltier-type thermoelectric device. Thus, the application of an electrical current to the preferred cooling system 14 causes the cold surface 14a to cool and causes the opposing hot surface 14b to heat up. The cooling system 14 cools the window assembly 12 via the situation of the window assembly 12 in thermally conductive relation to the cold surface 14a of the cooling system 14. It is contemplated that the cooling system 14, the heater layer 34, or both, can be operated to induce a desired time-varying temperature in the window assembly 12 to create an oscillating thermal gradient in the sample S, in accordance with various analyte-detection methodologies discussed herein.

Preferably, the cold reservoir 16 is positioned between the cooling system 14 and the window assembly 12, and functions as a thermal conductor between the system 14 and the window assembly 12. The cold reservoir 16 is formed from a suitable thermally conductive material, preferably brass. Alternatively, the window assembly 12 can be situated in direct contact with the cold surface 14a of the cooling system 14.

In alternative embodiments, the cooling system 14 may comprise a heat exchanger through which a coolant, such as air, nitrogen or chilled water, is pumped, or a passive conduction cooler such as a heat sink. As a further alternative, a gas coolant such as nitrogen may be circulated through the interior of the noninvasive system 10 so as to contact the underside of the window assembly 12 (see FIG. 1) and conduct heat therefrom.

Figure 4:
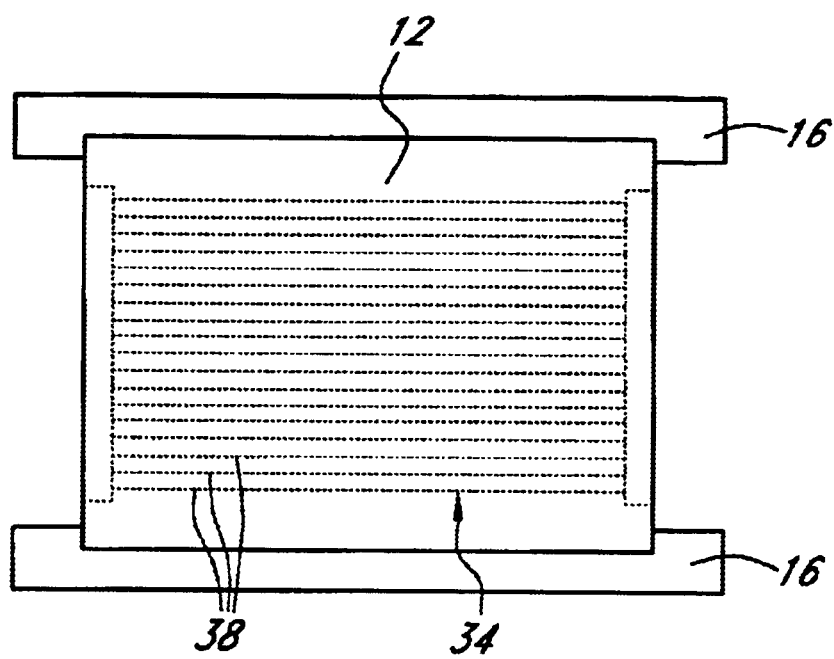
FIG. 4 is a plan view of the window assembly connected to a cooling system.
Figure 5:
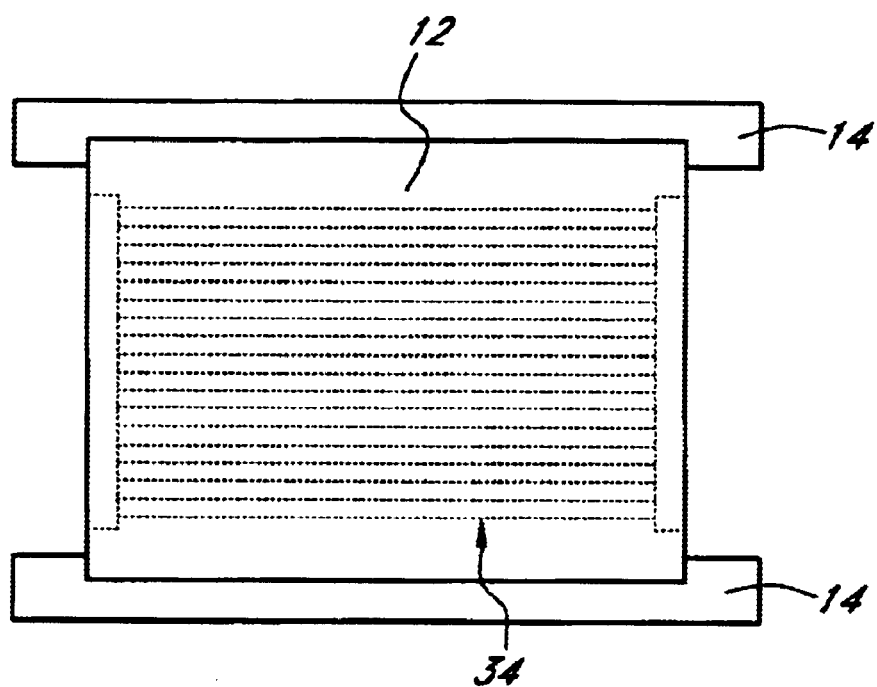
FIG. 5 is a plan view of the window assembly connected to a cold reservoir.

FIG. 4 is a top schematic view of a preferred arrangement of the window assembly 12 (of the type shown in FIG. 2) and the cold reservoir 16, and FIG. 5 is a top schematic view of an alternative arrangement in which the window assembly 12 directly contacts the cooling system 14. The cold reservoir 16/cooling system 14 preferably contacts the underside of the window assembly 12 along opposing edges thereof, on either side of the heater layer 34. With thermal conductivity thus established between the window assembly 12 and the cooling system 14, the window assembly can be cooled as needed during operation of the noninvasive system 10. In order to promote a substantially uniform or isothermal temperature profile over the upper surface of the window assembly 12, the pitch distance between centerlines of adjacent heater elements 38 may be made smaller (thereby increasing the density of heater elements 38) near the region(s) of contact between the window assembly 12 and the cold reservoir 16/cooling system 14. As a supplement or alternative, the heater elements 38 themselves may be made wider near these regions of contact. As used herein, "isothermal" is a broad term and is used in its ordinary sense and refers, without limitation, to a condition in which, at a given point in time, the temperature of the window assembly 12 or other structure is substantially uniform across a surface intended for placement in thermally conductive relation to the material sample S. Thus, although the temperature of the structure or surface may fluctuate over time, at any given point in time the structure or surface may nonetheless be isothermal.

The heat sink 18 drains waste heat from the hot surface 14b of the cooling system 16 and stabilizes the operational temperature of the noninvasive system 10. The preferred heat sink 18 (see FIG. 6) comprises a hollow structure formed from brass or any other suitable material having a relatively high specific heat and high heat conductivity. The heat sink 18 has a conduction surface 18a which, when the heat sink 18 is installed in the noninvasive system 18, is in thermally conductive relation to the hot surface 14b of the cooling system 14 (see FIG. 1). A cavity 54 is formed in the heat sink 18 and preferably contains a phase-change material (not shown) to increase the capacity of the sink 18. A preferred phase change material is a hydrated salt, such as calciumchloride hexahydrate, available under the name TH29 from PCM Thermal Solutions, Inc., of Naperville, Ill. Alternatively, the cavity 54 may be omitted to create a heat sink 18 comprising a solid, unitary mass. The heat sink 18 also forms a number of fins 56 to further increase the conduction of heat from the sink 18 to surrounding air.

Alternatively, the heat sink 18 may be formed integrally with the optical mixer 20 and/or the collimator 22 as a unitary mass of rigid, heat-conductive material such as brass or aluminum. In such a heat sink, the mixer 20 and/or collimator 22 extend axially through the heat sink 18, and the heat sink defines the inner walls of the mixer 20 and/or collimator 22. These inner walls are coated and/or polished to have appropriate reflectivity and nonabsorbance in infrared wavelengths as will be further described below. Where such a unitary heat sink-mixer-collimator is employed, it is desirable to thermally insulate the detector array from the heat sink.

It should be understood that any suitable structure may be employed to heat and/or cool the material sample S, instead of or in addition to the window assembly 12/cooling system 14 disclosed above, so long a proper degree of cycled heating and/or cooling are imparted to the material sample S. In addition other forms of energy, such as but not limited to light, radiation, chemically induced heat, friction and vibration, may be employed to heat the material sample S. It will be further appreciated that heating of the sample can achieved by any suitable method, such as convection, conduction, radiation, etc.

c. Optics

As shown in FIG. 1, the optical mixer 20 comprises a light pipe with an inner surface coating which is highly reflective and minimally absorptive in infrared wavelengths, preferably a polished gold coating, although other suitable coatings may be used where other wavelengths of electromagnetic radiation are employed. The pipe itself may be fabricated from a another rigid material such as aluminum or stainless steel, as long as the inner surfaces are coated or otherwise treated to be highly reflective. Preferably, the optical mixer 20 has a rectangular cross-section (as taken orthogonal to the longitudinal axis A—A of the mixer 20 and the collimator 22), although other cross-sectional shapes, such as other polygonal shapes or circular or elliptical shapes, may be employed in alternative embodiments. The inner walls of the optical mixer 20 are substantially parallel to the longitudinal axis A—A of the mixer 20 and the collimator 22. The highly reflective and substantially parallel inner walls of the mixer 20 maximize the number of times the infrared energy E will be reflected between the walls of the mixer 20, thoroughly mixing the infrared energy E as it propagates through the mixer 20. In a presently preferred embodiment, the mixer 20 is about 1.2 inches to 2.4 inches in length and its cross-section is a rectangle of about 0.4 inches by about 0.6 inches. Of course, other dimensions may be employed in constructing the mixer 20. In particular it is be advantageous to miniaturize the mixer or otherwise make it as small as possible Still referring to FIG. 1, the collimator 22 comprises a tube with an inner surface coating which is highly reflective and minimally absorptive in infrared wavelengths, preferably a polished gold coating. The tube itself may be fabricated from a another rigid material such as aluminum, nickel or stainless steel, as long as the inner surfaces are coated or otherwise treated to be highly reflective. Preferably, the collimator 22 has a rectangular cross-section, although other cross-sectional shapes, such as other polygonal shapes or circular, parabolic or elliptical shapes, may be employed in alternative embodiments. The inner walls of the collimator 22 diverge as they extend away from the mixer 20. Preferably, the inner walls of the collimator 22 are substantially straight and form an angle of about 7 degrees with respect to the longitudinal axis A—A. The collimator 22 aligns the infrared energy E to propagate in a direction that is generally parallel to the longitudinal axis A—A of the mixer 20 and the collimator 22, so that the infrared energy E will strike the surface of the filters 24 at an angle as close to 90 degrees as possible.

In a presently preferred embodiment, the collimator is about 7.5 inches in length. At its narrow end 22a, the cross-section of the collimator 22 is a rectangle of about 0.4 inches by 0.6 inches. At its wide end 22b, the collimator 22 has a rectangular cross-section of about 1.8 inches by 2.6 inches. Preferably, the collimator 22 aligns the infrared energy E to an angle of incidence (with respect to the longitudinal axis A—A) of about 0–15 degrees before the energy E impinges upon the filters 24. Of course, other dimensions or incidence angles may be employed in constructing and operating the collimator 22.

Figure 6:
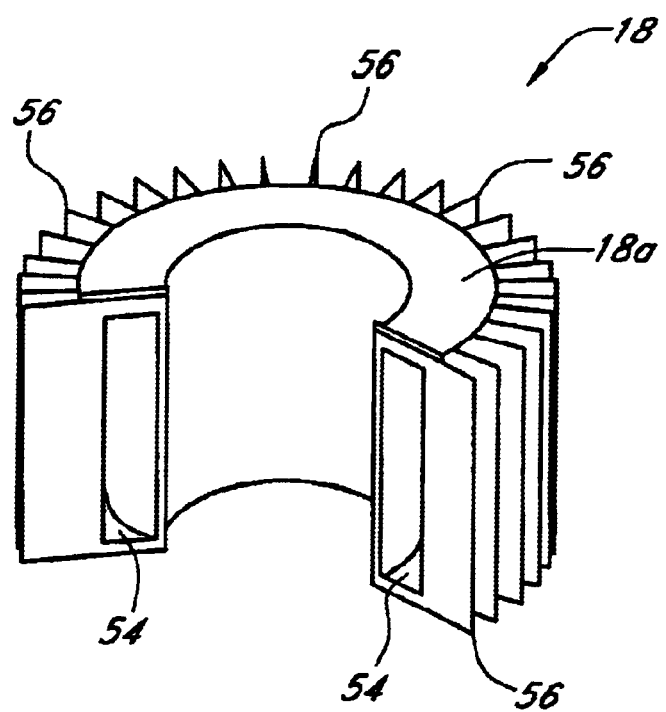
FIG. 6 is a cutaway view of a heat sink for use with the noninvasive detection system.
Figure 6A:
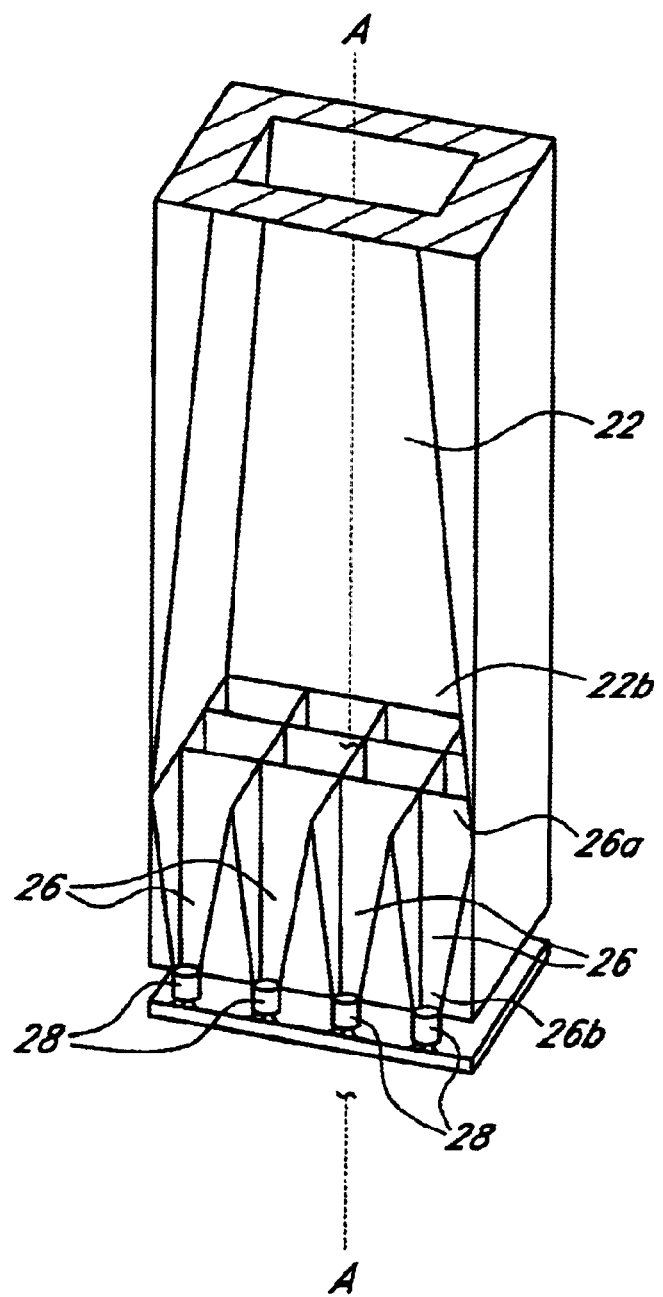
FIG. 6A is a cutaway perspective view of a lower portion of the noninvasive detection system of FIG. 1.

With further reference to FIGS. 1 and 6A, each concentrator 26 comprises a tapered surface oriented such that its wide end 26a is adapted to receive the infrared energy exiting the corresponding filter 24, and such that its narrow end 26b is adjacent to the corresponding detector 28. The inward-facing surfaces of the concentrators 26 have an inner surface coating which is highly reflective and minimally absorptive in infrared wavelengths, preferably a polished gold coating. The concentrators 26 themselves may be fabricated from a another rigid material such as aluminum, nickel or stainless steel, so long as their inner surfaces are coated or otherwise treated to be highly reflective.

Preferably, the concentrators 26 have a rectangular cross-section (as taken orthogonal to the longitudinal axis A—A), although other cross-sectional shapes, such as other polygonal shapes or circular, parabolic or elliptical shapes, may be employed in alternative embodiments. The inner walls of the concentrators converge as they extend toward the narrow end 26b. Preferably, the inner walls of the collimators 26 are substantially straight and form an angle of about 8 degrees with respect to the longitudinal axis A—A. Such a configuration is adapted to concentrate infrared energy as it passes through the concentrators 26 from the wide end 26a to the narrow end 26b, before reaching the detectors 28.

In a presently preferred embodiment, each concentrator 26 is about 1.5 inches in length. At the wide end 26a, the cross-section of each concentrator 26 is a rectangle of about 0.6 inches by 0.57 inches. At the narrow end 26b, each concentrator 26 has a rectangular cross-section of about 0.177 inches by 0.177 inches. Of course, other dimensions or incidence angles may be employed in constructing the concentrators 26.

d. Filters

The filters 24 preferably comprise standard interference-type infrared filters, widely available from manufacturers such as Optical Coating Laboratory, Inc. ("OCLI") of Santa Rosa, Calif. In the embodiment illustrated in FIG. 1, a 3×4 array of filters 24 is positioned above a 3×4 array of detectors 28 and concentrators 26. As employed in this embodiment, the filters 24 are arranged in four groups of three filters having the same wavelength sensitivity. These four groups have bandpass center wavelengths of 7.15 $\mu$m±0.03 $\mu$m, 8.40 $\mu$m±0.03 $\mu$m, 9.48 $\mu$m±0.04 $\mu$m, and 11.10 $\mu$m±0.04 $\mu$m, respectively, which correspond to wavelengths around which water and glucose absorb electromagnetic radiation. Typical bandwidths for these filters range from 0.20 $\mu$m to 0.50 $\mu$m.

In an alternative embodiment, the array of wavelength-specific filters 24 may be replaced with a single Fabry-Perot interferometer, which can provide wavelength sensitivity which varies as a sample of infrared energy is taken from the material sample S. Thus, this embodiment permits the use of only one detector 28, the output signal of which varies in wavelength specificity over time. The output signal can be de-multiplexed based on the wavelength sensitivities induced by the Fabry-Perot interferometer, to provide a multiple-wavelength profile of the infrared energy emitted by the material sample S. In this embodiment, the optical mixer 20 may be omitted, as only one detector 28 need be employed.

In still other embodiments, the array of filters 24 may comprise a filter wheel that rotates different filters with varying wavelength sensitivities over a single detector 24. Alternatively, an electronically tunable infrared filter may be employed in a manner similar to the Fabry-Perot interferometer discussed above, to provide wavelength sensitivity which varies during the detection process. In either of these embodiments, the optical mixer 20 may be omitted, as only one detector 28 need be employed.

e. Detectors

The detectors 28 may comprise any detector type suitable for sensing infrared energy, preferably in the mid-infrared wavelengths. For example, the detectors 28 may comprise mercury-cadmium-telluride (MCT) detectors. A detector such as a Fermionics (Simi Valley, Calif.) model PV-9.1 with a PVA481-1 pre-amplifier is acceptable. Similar units from other manufacturers such as Graseby (Tampa, Fla.) can be substituted. Other suitable components for use as the detectors 28 include pyroelectric detectors, thermopiles, bolometers, silicon microbolometers and lead-salt focal plane arrays.

f. Control System

Figure 7:
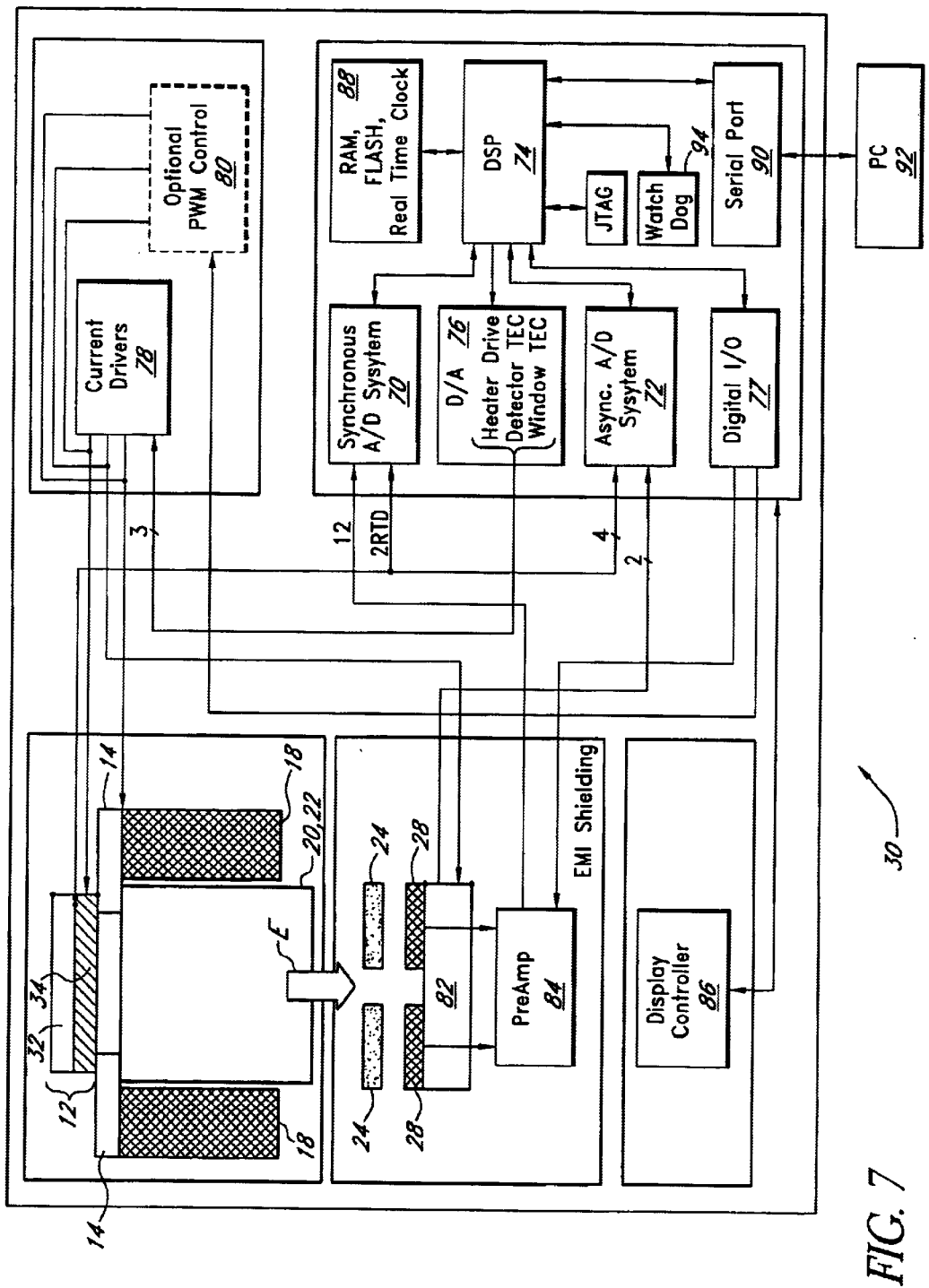
FIG. 7 is a schematic view of a control system for use with the noninvasive optical detection system.

FIG. 7 depicts the control system 30 in greater detail, as well as the interconnections between the control system and other relevant portions of the noninvasive system. The control system includes a temperature control subsystem and a data acquisition subsystem.

In the temperature control subsystem, temperature sensors (such as RTDs and/or thermistors) located in the window assembly 12 provide a window temperature signal to a synchronous analog-to-digital conversion system 70 and an asynchronous analog-to-digital conversion system 72. The A/D systems 70, 72 in turn provide a digital window temperature signal to a digital signal processor (DSP) 74. The processor 74 executes a window temperature control algorithm and determines appropriate control inputs for the heater layer 34 of the window assembly 12 and/or for the cooling system 14, based on the information contained in the window temperature signal. The processor 74 outputs one or more digital control signals to a digital-to-analog conversion system 76 which in turn provides one or more analog control signals to current drivers 78. In response to the control signal(s), the current drivers 78 regulate the power supplied to the heater layer 34 and/or to the cooling system 14. In one embodiment, the processor 74 provides a control signal through a digital I/O device 77 to a pulse-width modulator (PWM) control 80, which provides a signal that controls the operation of the current drivers 78. Alternatively, a low-pass filter (not shown) at the output of the PWM provides for continuous operation of the current drivers 78.

In another embodiment, temperature sensors may be located at the cooling system 14 and appropriately connected to the A/D system(s) and processor to provide closed-loop control of the cooling system as well.

In yet another embodiment, a detector cooling system 82 is located in thermally conductive relation to one or more of the detectors 28. The detector cooling system 82 may comprise any of the devices disclosed above as comprising the cooling system 14, and preferably comprises a Peltier-type thermoelectric device. The temperature control subsystem may also include temperature sensors, such as RTDs and/or thermistors, located in or adjacent to the detector cooling system 82, and electrical connections between these sensors and the asynchronous A/D system 72. The temperature sensors of the detector cooling system 82 provide detector temperature signals to the processor 74. In one embodiment, the detector cooling system 82 operates independently of the window temperature control system, and the detector cooling system temperature signals are sampled using the asynchronous A/D system 72. In accordance with the temperature control algorithm, the processor 74 determines appropriate control inputs for the detector cooling system 82, based on the information contained in the detector temperature signal. The processor 74 outputs digital control signals to the D/A system 76 which in turn provides analog control signals to the current drivers 78. In response to the control signals, the current drivers 78 regulate the power supplied to the detector cooling system 14. In one embodiment, the processor 74 also provides a control signal through the digital I/O device 77 and the PWM control 80, to control the operation of the detector cooling system 82 by the current drivers 78. Alternatively, a low-pass filter (not shown) at the output of the PWM provides for continuous operation of the current drivers 78.

In the data acquisition subsystem, the detectors 28 respond to the infrared energy E incident thereon by passing one or more analog detector signals to a preamp 84. The preamp 84 amplifies the detector signals and passes them to the synchronous A/D system 70, which converts the detector signals to digital form and passes them to the processor 74. The processor 74 determines the concentrations of the analyte(s) of interest, based on the detector signals and a concentration-analysis algorithm and/or phase/concentration regression model stored in a memory module 88. The concentration-analysis algorithm and/or phase/concentration regression model may be developed according to any of the analysis methodologies discussed herein. The processor may communicate the concentration results and/or other formation to a display controller 86, which operates a display (not shown), such as an LCD display, to present the information to the user.

A watchdog timer 94 may be employed to ensure that the processor 74 is operating correctly. If the watchdog timer 94 does not receive a signal from the processor 74 within a specified time, the watchdog timer 94 resets the processor 74. The control system may also include a JTAG interface 96 to enable testing of the noninvasive system 10.

In one embodiment, the synchronous A/D system 70 comprises a 20-bit, 14 channel system, and the asynchronous A/D system 72 comprises a 16-bit, 16 channel system. The preamp may comprise a 12-channel preamp corresponding to an array of 12 detectors 28.

The control system may also include a serial port 90 or other conventional data port to permit connection to a personal computer 92. The personal computer can be employed to update the algorithm(s) and/or phase/concentration regression model(s) stored in the memory module 88, or to download a compilation of analyte-concentration data from the noninvasive system. A real-time clock or other timing device may be accessible by the processor 74 to make any time-dependent calculations which may be desirable to a user.

2. Analysis Methodology

The detector(s) 28 of the noninvasive system 10 are used to detect the infrared energy emitted by the material sample S in various desired wavelengths. At each measured wavelength, the material sample S emits infrared energy at an intensity which varies over time. The time-varying intensities arise largely in response to the use of the window assembly 12 (including its heater layer 34) and the cooling system 14 to induce a thermal gradient in the material sample S. As used herein, "thermal gradient" is a broad term and is used in its ordinary sense and refers, without limitation, to a difference in temperature and/or thermal energy between different locations, such as different depths, of a material sample, which can be induced by any suitable method of increasing or decreasing the temperature and/or thermal energy in one or more locations of the sample. As will be discussed in detail below, the concentration of an analyte of interest (such as glucose) in the material sample S can be determined with a device such as the noninvasive system 10, by comparing the time-varying intensity profiles of the various measured wavelengths.

Analysis methodologies are discussed herein within the context of detecting the concentration of glucose within a material sample, such as a tissue sample, which includes a large proportion of water. However, it will evident that these methodologies are not limited to this context and may be applied to the detection of a wide variety of analytes within a wide variety of sample types. It should also be understood that other suitable analysis methodologies and suitable variations of the disclosed methodologies may be employed in operating an analyte detection system, such as the non-invasive system 10.

Figure 8:
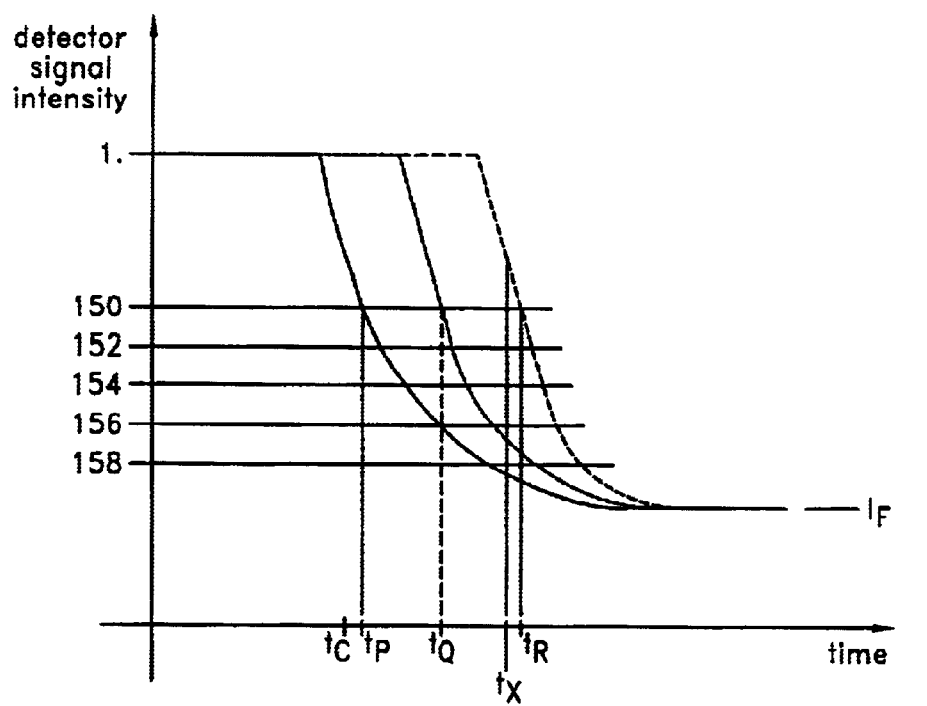
FIG. 8 depicts a first methodology for determining the concentration interest.

As shown in FIG. 8, a first reference signal P may be measured at a first reference wavelength. The first reference signal P is measured at a wavelength where water strongly absorbs (e.g., 2.9 $\mu$m or 6.1 $\mu$m). Because water strongly absorbs radiation at these wavelengths, the detector signal intensity is reduced at those wavelengths. Moreover, at these wavelengths water absorbs the photon emissions emanating from deep inside the sample. The net effect is that a signal emitted at these wavelengths from deep inside the sample is not easily detected. The first reference signal P is thus a good indicator of thermal-gradient effects near the sample surface and may be known as a surface reference signal. This signal may be calibrated and normalized, in the absence of heating or cooling applied to the sample, to a baseline value of 1. For greater accuracy, more than one first reference wavelength may be measured. For example, both 2.9 μm and 6.1 μm may be chosen as first reference wavelengths.

As further shown in FIG. 8, a second reference signal R may also be measured. The second signal R may be measured at a wavelength where water has very low absorbance (e.g., 3.6 μm or 4.2 μm). This second reference signal R thus provides the analyst with information concerning the deeper regions of the sample, whereas the first signal P provides information concerning the sample surface. This signal may also be calibrated and normalized, in the absence of heating or cooling applied to the sample, to a baseline value of 1. As with the first (surface) reference signal P, greater accuracy may be obtained by using more than one second (deep) reference signal R.

In order to determine analyte concentration, a third (analytical) signal Q is also measured. This signal is measured at an IR absorbance peak of the selected analyte. The IR absorbance peaks for glucose are in the range of about 6.5 μm to 11.0 μm. This detector signal may also be calibrated and normalized, in the absence of heating or cooling applied to the material sample S, to a baseline value of 1. As with the reference signals P, R, the analytical signal Q may be measured at more than one absorbance peak.

Optionally, or additionally, reference signals may be measured at wavelengths that bracket the analyte absorbance peak. These signals may be advantageously monitored at reference wavelengths which do not overlap the analyte absorbance peaks. Further, it is advantageous to measure reference wavelengths at absorbance peaks which do not overlap the absorbance peaks of other possible constituents contained in the sample.

a. Basic Thermal Gradient

As further shown in FIG. 8, the signal intensities P, Q, R are shown initially at the normalized baseline signal intensity of 1. This of course reflects the baseline radiative behavior of a test sample in the absence of applied heating or cooling. At a time $t_C$, the surface of the sample is subjected to a temperature event which induces a thermal gradient in the sample. The gradient can be induced by heating or cooling the sample surface The example shown in FIG. 8 uses cooling, for example, using a 10° C. cooling event. In response to the cooling event, the intensities of the detector signals P, Q, R decrease over time.

Since the cooling of the sample is neither uniform nor instantaneous, the surface cools before the deeper regions of the sample cool. As each of the signals P, Q, R drop in intensity, a pattern emerges. Signal intensity declines as expected, but as the signals P, Q, R reach a given amplitude value (or series of amplitude values: 150, 152, 154, 156, 158), certain temporal effects are noted. After the cooling event is induced at $t_C$, the first (surface) reference signal P declines in amplitude most rapidly, reaching a checkpoint 150 first, at time $t_P$. This is due to the fact that the first reference signal P mirrors the sample's radiative characteristics near the surface of the sample. Since the sample surface cools before the underlying regions, the surface (first) reference signal P drops in intensity first.

Simultaneously, the second reference signal R is monitored. Since the second reference signal R corresponds to the radiation characteristics of deeper regions of the sample, which do not cool as rapidly as the surface (due to the time needed for the surface cooling to propagate into the deeper regions of the sample), the intensity of signal R does not decline until slightly later. Consequently, the signal R does not reach the magnitude 150 until some later time $t_R$. In other words, there exists a time delay between the time $t_P$ at which the amplitude of the first reference signal P reaches the checkpoint 150 and the time $t_R$ at which the second reference signal R reaches the same checkpoint 150. This time delay can be expressed as a phase difference $\Phi(\lambda)$. Additionally, a phase difference may be measured between the analytical signal Q and either or both reference signals P, R.

As the concentration of analyte increases, the amount of absorbance at the analytical wavelength increases. This reduces the intensity of the analytical signal Q in a concentration-dependent way. Consequently, the analytical signal Q reaches intensity 150 at some intermediate time $t_Q$. The higher the concentration of analyte, the more the analytical signal Q shifts to the left in FIG. 8. As a result, with increasing analyte concentration, the phase difference $\Phi(\lambda)$ decreases relative to the first (surface) reference signal P and increases relative to the second (deep tissue) reference signal R. The phase difference(s) $\Phi(\lambda)$ are directly related to analyte concentration and can be used to make accurate determinations of analyte concentration.

The phase difference $\Phi(\lambda)$ between the first (surface) reference signal P and the analytical signal Q is represented by the equation:

$$\Phi(\lambda)=|t_P-t_Q|$$

The magnitude of this phase difference decreases with increasing analyte concentration.

The phase difference $\Phi(\lambda)$ between the second (deep tissue) reference signal R and the analytical signal Q signal is represented by the equation:

$$\Phi(\lambda)=|t_Q-t_R|$$

The magnitude of this phase difference increases with increasing analyte concentration.

Accuracy may be enhanced by choosing several checkpoints, for example, 150, 152, 154, 156, and 158 and averaging the phase differences observed at each checkpoint. The accuracy of this method may be further enhanced by integrating the phase difference(s) continuously over the entire test period. Because in this example only a single temperature event (here, a cooling event) has been induced, the sample reaches a new lower equilibrium temperature and the signals stabilize at a new constant level $I_F$. Of course, the method works equally well with thermal gradients induced by heating or by the application or introduction of other forms of energy, such as but not limited to, light, radiation, chemically induced heat, friction and vibration.

This methodology is not limited to the determination of phase difference. At any given time (for example, at a time $t_X$) the amplitude of the analytical signal Q may be compared to the amplitude of either or both of the reference signals P, R. The difference in amplitude may be observed and processed to determine analyte concentration.

This method, the variants disclosed herein, and the apparatus disclosed as suitable for application of the method(s), are not limited to the detection of in-vivo glucose concentration. The method and disclosed variants and apparatus may be used on human, animal, or even plant subjects, or on organic or inorganic compositions in a non-medical setting. The method may be used to take measurements of in-vivo or in-vitro samples of virtually any kind. The method is useful for measuring the concentration of a wide range of additional chemical analytes, including but not limited to, glucose, ethanol, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, cytochrome, various proteins and chromophores, microcalcifications, hormones, as well as other chemical compounds. To detect a given analyte, one needs only to select appropriate analytical and reference wavelengths.

The method is adaptable and may be used to determine chemical concentrations in samples of body fluids (e.g., blood, urine or saliva) once they have been extracted from a patient. In fact, the method may be used for the measurement of in-vitro samples of virtually any kind.

b. Modulated Thermal Gradient

In a variation of the methodology described above, a periodically modulated thermal gradient can be employed to make accurate determinations of analyte concentration.

As previously shown in FIG. 8, once a thermal gradient is induced in the sample, the reference and analytical signals P, Q, R fall out of phase with respect to each other. This phase difference $\Phi(\lambda)$ is present whether the thermal gradient is induced through heating or cooling. By alternatively subjecting the test sample to cyclic pattern of heating, cooling, or alternately heating and cooling, an oscillating thermal gradient may be induced in a sample for an extended period of time.

Figure 9:
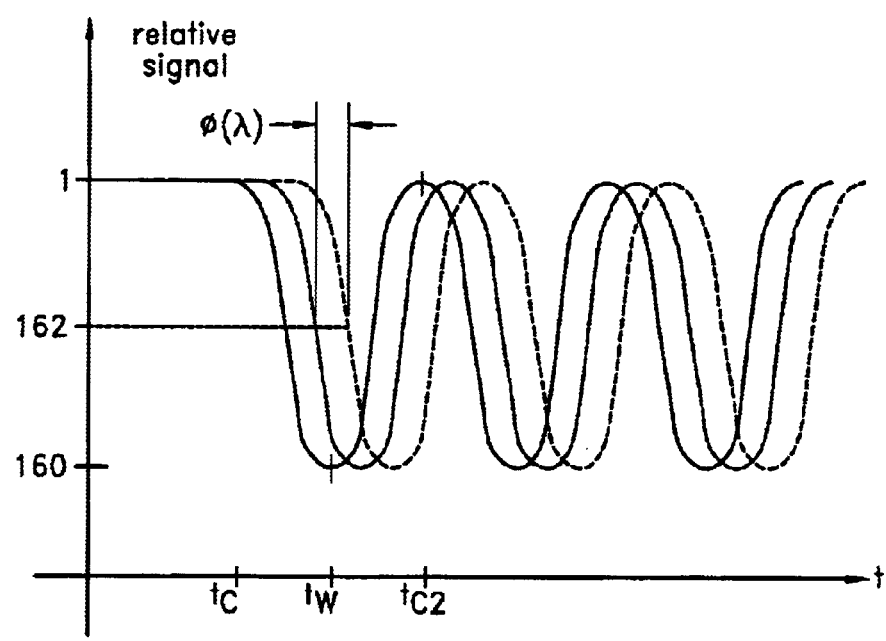
FIG. 9 depicts a second methodology for determining the an analyte of interest.

An oscillating thermal gradient is illustrated using a sinusoidally modulated gradient. FIG. 9 depicts detector signals emanating from a test sample. As with the methodology shown in FIG. 8, one or more reference signals J, L are measured. One or more analytical signals K are also monitored. These signals may be calibrated and normalized, in the absence of heating or cooling applied to the sample, to a baseline value of 1. FIG. 9 shows the signals after normalization. At some time $t_C$, a temperature event (e.g., cooling) is induced at the sample surface. This causes a decline in the detector signal. As shown in FIG. 8, the signals (P, Q, R) decline until the thermal gradient disappears and a new equilibrium detector signal $I_F$ is reached. In the method shown in FIG. 9, as the gradient begins to disappear at a signal intensity 160, a heating event, at a time $t_W$, is induced in the sample surface. As a result the detector output signals J, K, L will rise as the sample temperature rises. At some later time $t_{C2}$, another cooling event is induced, causing the temperature and detector signals to decline. This cycle of cooling and heating may be repeated over a time interval of arbitrary length. Moreover, if the cooling and heating events are timed properly, a periodically modulated thermal gradient may be induced in the test sample.

As previously explained in the discussions relating to FIG. 8, the phase difference $\Phi(\lambda)$ may be measured and used to determine analyte concentration. FIG. 9 shows that the first (surface) reference signal J declines and rises in intensity first. The second (deep tissue) reference signal L declines and rises in a time-delayed manner relative to the first reference signal J. The analytical signal K exhibits a time/phase delay dependent on the analyte concentration. With increasing concentration, the analytical signal K shifts to the left in FIG. 9. As with FIG. 8, the phase difference $\Phi(\lambda)$ may be measured. For example, a phase difference $\Phi(\lambda)$ between the second reference signal L and the analytical signal K, may be measured at a set amplitude 162 as shown in FIG. 9. Again, the magnitude of the phase signal reflects the analyte concentration of the sample.

The phase-difference information compiled by any of the methodologies disclosed herein can correlated by the control system 30 (see FIG. 1) with previously determined phase-difference information to determine the analyte concentration in the sample. This correlation could involve comparison of the phase-difference information received from analysis of the sample, with a data set containing the phase-difference profiles observed from analysis of wide variety of standards of known analyte concentration. In one embodiment, a phase/concentration curve or regression model is established by applying regression techniques to a set of phase-difference data observed in standards of known analyte concentration. This curve is used to estimate the analyte concentration in a sample based on the phase-difference information received from the sample.

Advantageously, the phase difference $\Phi(\lambda)$ may be measured continuously throughout the test period. The phase-difference measurements may be integrated over the entire test period for an extremely accurate measure of phase difference $\Phi(\lambda)$. Accuracy may also be improved by using more than one reference signal and/or more than one analytical signal.

As an alternative or as a supplement to measuring phase difference(s), differences in amplitude between the analytical and reference signal(s) may be measured and employed to determine analyte concentration. Additional details relating to this technique and not necessary to repeat here may be found in the Assignee's U.S. patent application Ser. No. 09/538,164, incorporated by reference below.

Additionally, these methods may be advantageously employed to simultaneously measure the concentration of one or more analytes. By choosing reference and analyte wavelengths that do not overlap, phase differences can be simultaneously measured and processed to determine analyte concentrations. Although FIG. 9 illustrates the method used in conjunction with a sinusoidally modulated thermal gradient, the principle applies to thermal gradients conforming to any periodic function. In more complex cases, analysis using signal processing with Fourier transforms or other techniques allows accurate determinations of phase difference $\Phi(\lambda)$ and analyte concentration.

Figure 10:
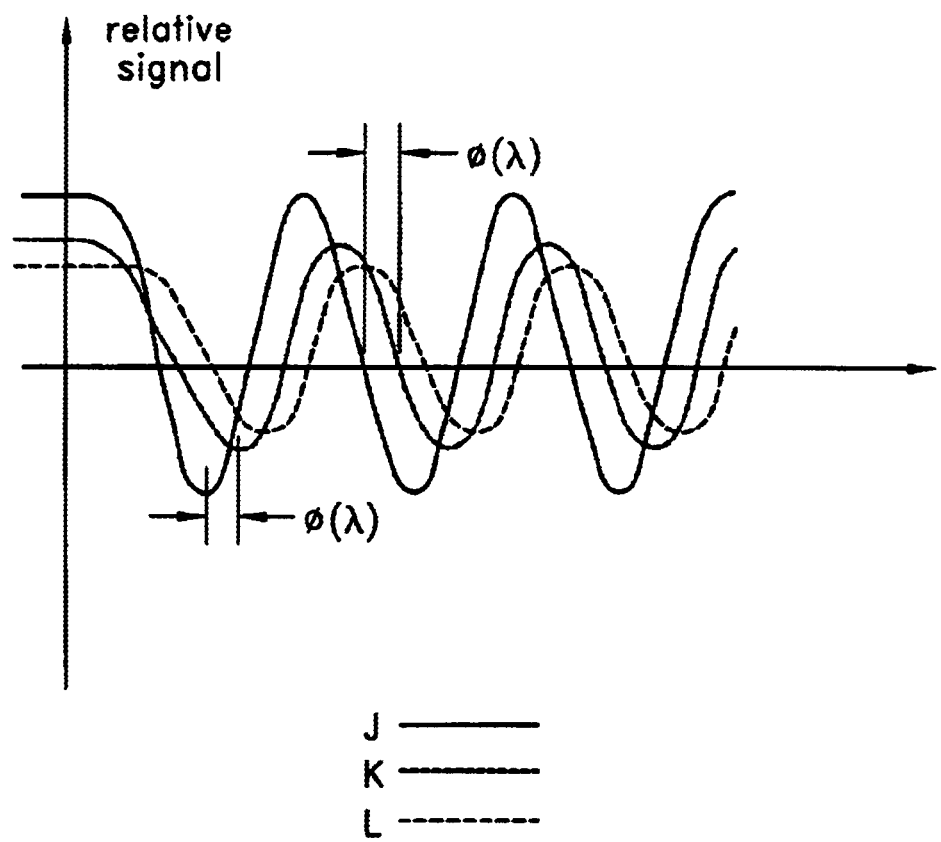
FIG. 10 depicts a third methodology for determining the concentration interest.

As shown in FIG. 10, the magnitude of the phase differences may be determined by measuring the time intervals between the amplitude peaks (or troughs) of the reference signals J, L and the analytical signal K. Alternatively, the time intervals between the "zero crossings" (the point at which the signal amplitude changes from positive to negative, or negative to positive) may be used to determine the phase difference between the analytical signal K and the reference signals J, L. This information is subsequently processed and a determination of analyte concentration may then be made. This particular method has the advantage of not requiring normalized signals.

As a further alternative, two or more driving frequencies may be employed to determine analyte concentrations at selected depths within the sample. A slow (e.g., 1 Hz) driving frequency creates a thermal gradient which penetrates deeper into the sample than the gradient created by a fast (e.g., 3 Hz) driving frequency. This is because the individual heating and/or cooling events are longer in duration where the driving frequency is lower. Thus, the use of a slow driving frequency provides analyte-concentration information from a deeper "slice" of the sample than does the use of a fast driving frequency.

It has been found that when analyzing a sample of human skin, a temperature event of 10° C. creates a thermal gradient which penetrates to a depth of about 150 $\mu$m, after about 500 ms of exposure. Consequently, a cooling/heating cycle or driving frequency of 1 Hz provides information to a depth of about 150 $\mu$m. It has also been determined that exposure to a temperature event of 10° C. for about 167 ms creates a thermal gradient that penetrates to a depth of about 50 $\mu$m.

Therefore, a cooling/heating cycle of 3 Hz provides information to a depth of about 50 $\mu$m. By subtracting the detector signal information measured at a 3 Hz driving frequency from the detector signal information measured at a 1 Hz driving frequency, one can determine the analyte concentration(s) in the region of skin between 50 and 150 $\mu$m. Of course, a similar approach can be used to determine analyte concentrations at any desired depth range within any suitable type of sample.

Figure 11:
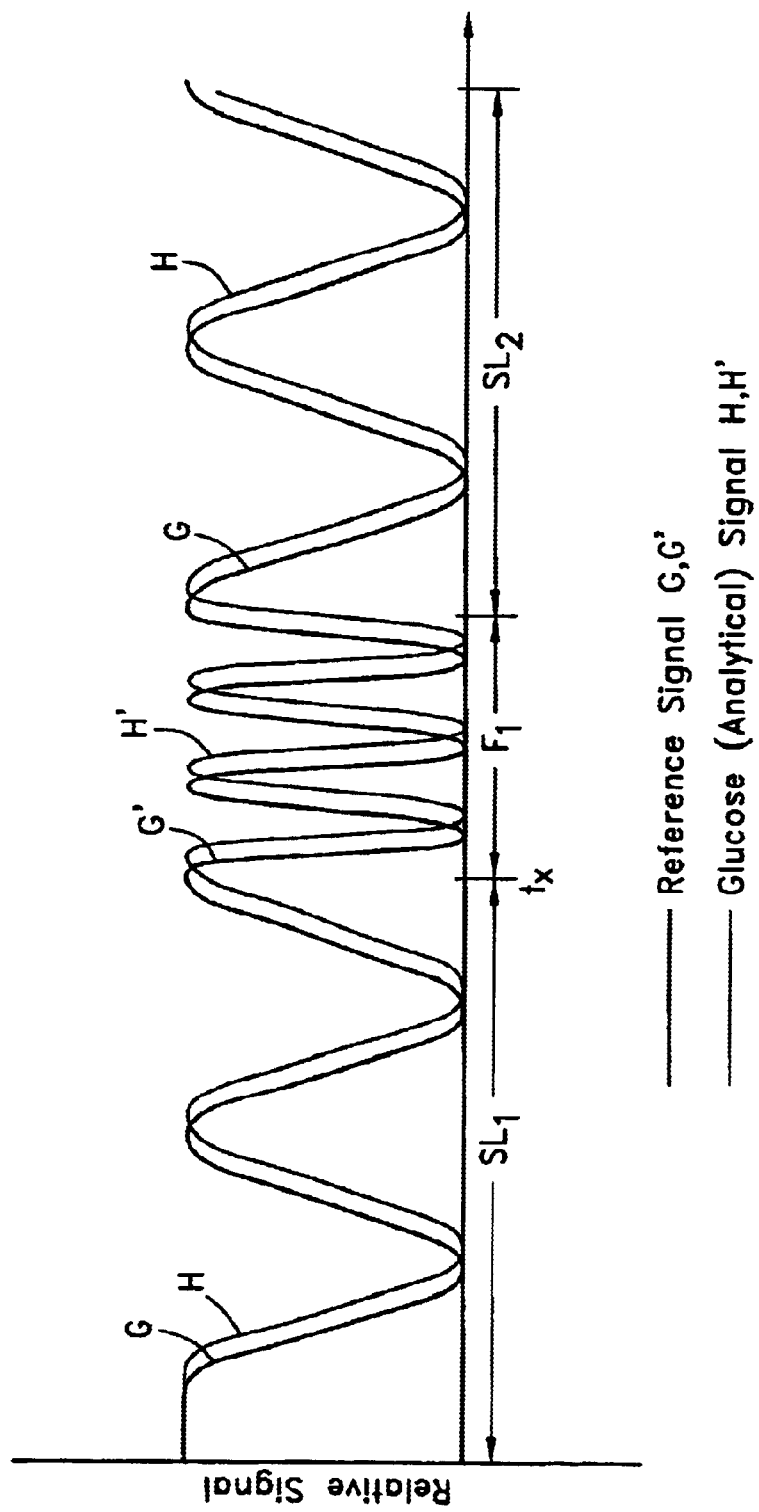
FIG. 11 depicts a fourth methodology for determining the an analyte of interest.

As shown in FIG. 11, alternating deep and shallow thermal gradients may be induced by alternating slow and fast driving frequencies. As with the methods described above, this variation also involves the detection and measurement of phase differences $\Phi(\lambda)$ between reference signals G, G' and analytical signals H, H'. Phase differences are measured at both fast (e.g., 3 Hz) and slow (e.g., 1 Hz) driving frequencies. The slow driving frequency may continue for an arbitrarily chosen number of cycles (in region $SL_1$), for example, two full cycles. Then the fast driving frequency is employed for a selected duration, in region $F_1$. The phase difference data is compiled in the same manner as disclosed above. In addition, the fast frequency (shallow sample) phase difference data may be subtracted from the slow frequency (deep sample) data to provide an accurate determination of analyte concentration in the region of the sample between the gradient penetration depth associated with the fast driving frequency and that associated with the slow driving frequency.

Figure 12:
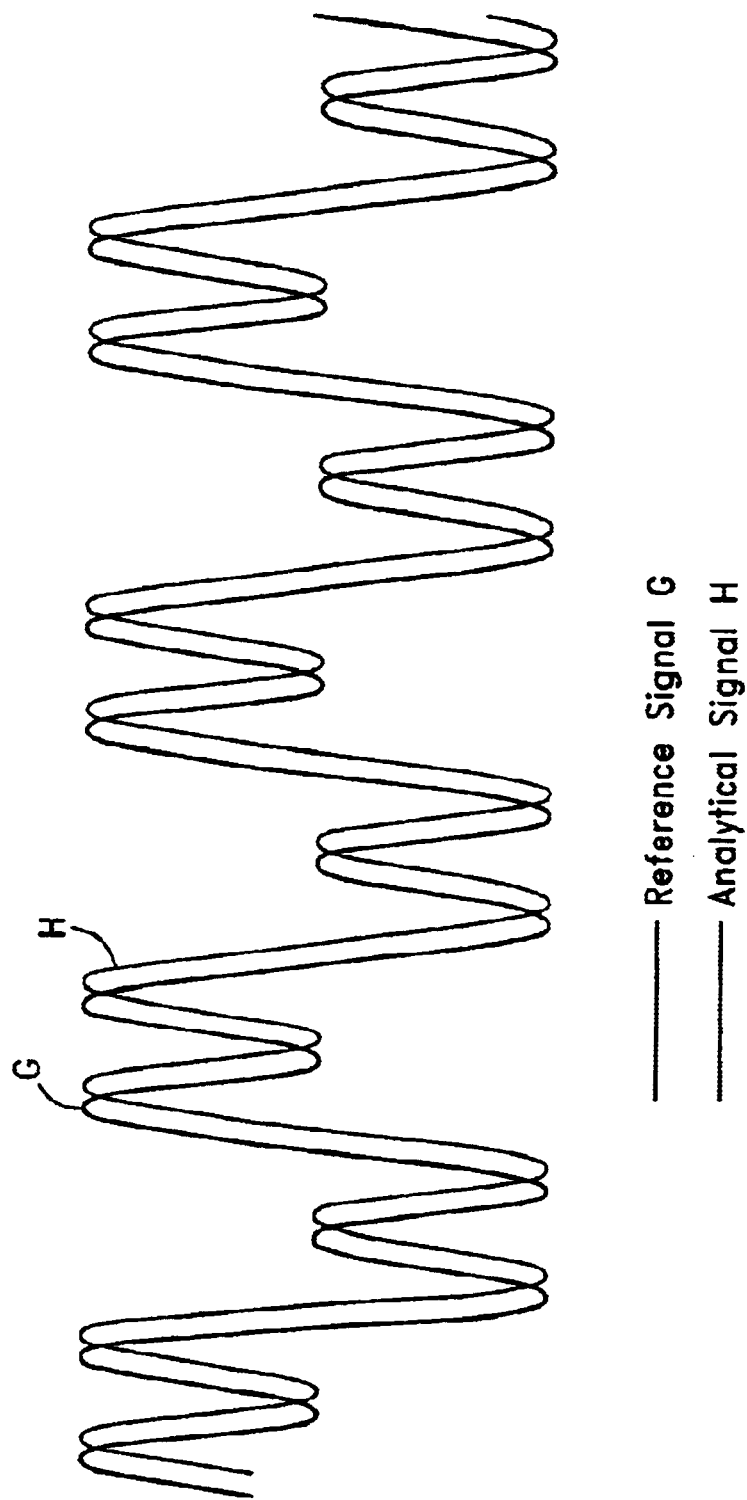
FIG. 12 depicts a fifth methodology for determining the concentration interest.

The driving frequencies (e.g., 1 Hz and 3 Hz) can be multiplexed as shown in FIG. 12. The fast (3 Hz) and slow (1 Hz) driving frequencies can be superimposed rather than sequentially implemented. During analysis, the data can be separated by frequency (using Fourier transform or other techniques) and independent measurements of phase delay at each of the driving frequencies may be calculated. Once resolved, the two sets of phase delay data are processed to determine absorbance and analyte concentration.

Additional details not necessary to repeat here may be found in U.S. Pat. No. 6,198,949, titled SOLID-STATE NON-INVASIVE INFRARED ABSORPTION SPECTROMETER FOR THE GENERATION AND CAPTURE OF THERMAL GRADIENT SPECTRA FROM LIVING TISSUE, issued Mar. 6, 2001; U.S. Pat. No. 6,161,028, titled METHOD FOR DETERMINING ANALYTE CONCENTRATION USING PERIODIC TEMPERATURE MODULATION AND PHASE DETECTION, issued Dec. 12, 2000; U.S. Pat. No. 5,877,500, titled MULTICHANNEL INFRARED DETECTOR WITH OPTICAL CONCENTRATORS FOR EACH CHANNEL, issued on Mar. 2, 1999; U.S. patent application Ser. No. 09/538,164, filed Mar. 30, 2000 and titled METHOD AND APPARATUS FOR DETERMINING ANALYTE CONCENTRATION USING PHASE AND MAGNITUDE DETECTION OF A RADIATION TRANSFER FUNCTION; U.S. patent application Ser. No. 09/427,178 (published as WIPO PCT Publication No. WO 01/30236 on May 3, 2001), filed Oct. 25, 1999, titled SOLID-STATE NON-INVASIVE THERMAL CYCLING SPECTROMETER; U.S. Provisional Patent Application No. 60/336,404, filed Oct. 29, 2001, titled WINDOW ASSEMBLY; U.S. Provisional Patent Application No. 60/340,794, filed Dec. 11, 2001, titled REAGENT-LESS WHOLE-BLOOD GLUCOSE METER; U.S. Provisional Patent Application No. 60/340,435, filed Dec. 12, 2001, titled CONTROL SYSTEM FOR BLOOD CONSTITUENT MONITOR; U.S. Provisional Patent Application No. 60/340,654, filed Dec. 12, 2001, titled SYSTEM AND METHOD FOR CONDUCTING AND DETECTING INFRARED RADIATION; U.S. Provisional Patent Application No. 60/340,773, filed Dec. 11, 2001, titled METHOD FOR TRANSFORMING PHASE SPECTRA TO ABSORPTION SPECTRA; U.S. Provisional Patent Application No. 60/332,322, filed Nov. 21, 2001, titled METHOD FOR ADJUSTING SIGNAL VARIATION OF AN ELECTRONICALLY CONTROLLED INFRARED TRANSMISSIVE WINDOW; U.S. Provisional Patent Application No. 60/332,093, filed Nov. 21, 2001, titled METHOD FOR IMPROVING THE ACCURACY OF AN ALTERNATE SITE BLOOD GLUCOSE MEASUREMENT; U.S. Provisional Patent Application No. 60/332,125, filed Nov. 21, 2001, titled METHOD FOR ADJUSTING A BLOOD ANALYTE MEASUREMENT; U.S. Provisional Patent Application No. 60/341,435, filed Dec. 14, 2001, titled PATHLENGTH-INDEPENDENT METHODS FOR OPTICALLY DETERMINING MATERIAL COMPOSITION; U.S. Provisional Patent Application No. 60/339,120, filed Dec. 7, 2001, titled QUADRATURE DEMODULATION AND KALMAN FILTERING IN A BIOLOGICAL CONSTITUENT MONITOR; U.S. Provisional Patent Application No. 60/339,044, filed Nov. 12, 2001, titled FAST SIGNAL DEMODULATION WITH MODIFIED PHASE-LOCKED LOOP TECHNIQUES; U.S. Provisional Patent Application No. 60/336,294, filed Oct. 29, 2001, titled METHOD AND DEVICE FOR INCREASING ACCURACY OF BLOOD CONSTITUENT MEASUREMENT; U.S. Provisional Patent Application No. 60/338,992, filed Nov. 13, 2001, titled SITE SELECTION FOR DETERMINING ANALYTE CONCENTRATION IN LIVING TISSUE; and U.S. Provisional Patent Application No. 60/339,116, filed Nov. 7, 2001, titled METHOD AND APPARATUS FOR IMPROVING CLINICALLY SIGNIFICANT ACCURACY OF ANALYTE MEASUREMENTS. The entire disclosure of all of the above-mentioned patents, patent applications and publications is hereby incorporated by reference herein and made a part of this specification.

B. Whole-Blood Detection System

Figure 13:
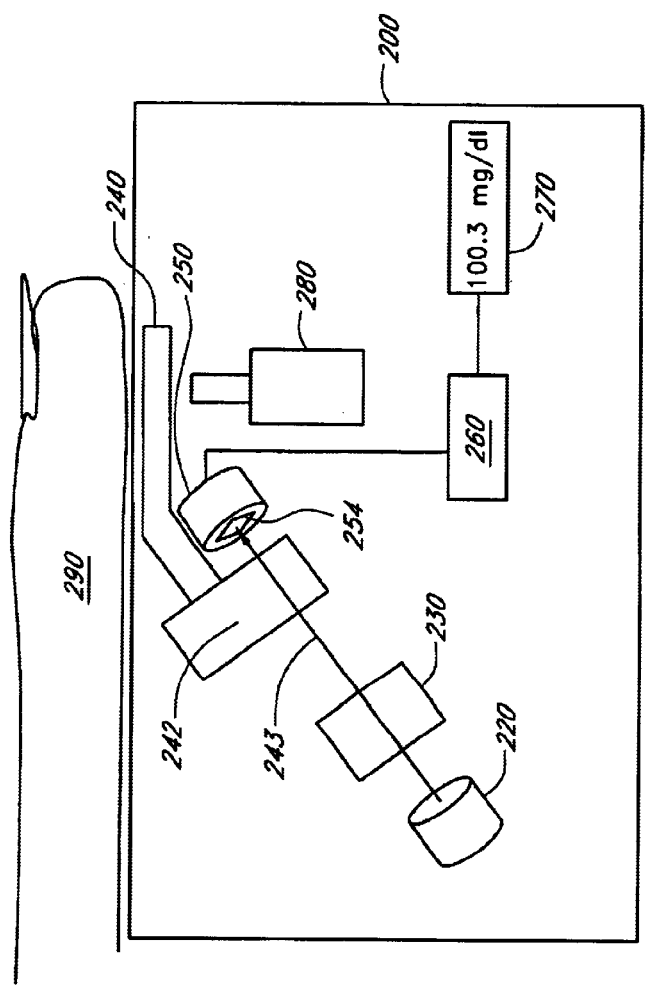
FIG. 13 is a schematic view of a reagentless whole-blood detection

FIG. 13 is a schematic view of a reagentless whole-blood analyte detection system 200 (hereinafter "whole-blood system") in a preferred configuration. The whole-blood system 200 may comprise a radiation source 220, a filter 230, a cuvette 240 that includes a sample cell 242, and a radiation detector 250. The whole-blood system 200 preferably also comprises a signal processor 260 and a display 270. Although a cuvette 240 is shown here, other sample elements, as described below, could also be used in the system 200. The whole-blood system 200 can also comprise a sample extractor 280, which can be used to access bodily fluid from an appendage, such as the finger 290, forearm, or any other suitable location As used herein, the terms "whole-blood analyte detection system" and "whole-blood system" are broad, synonymous terms and are used in their ordinary sense and refer, without limitation, to analyte detection devices which can determine the concentration of an analyte in a material sample by passing electromagnetic radiation through the sample and detecting the absorbance of the radiation by the sample. As used herein, the term "whole-blood" is a broad term and is used in its ordinary sense and refers, without limitation, to blood that has been withdrawn from a patient but that has not been otherwise processed, e.g., it has not been hemolysed, lyophilized, centrifuged, or separated in any other manner, after being removed from the patient. Whole-blood may contain amounts of other fluids, such as interstitial fluid or intracellular fluid, which may enter the sample during the withdrawal process or are naturally present in the blood. It should be understood, however, that the whole-blood system 200 disclosed herein is not limited to analysis of whole-blood, as the whole-blood system 10 may be employed to analyze other substances, such as saliva, urine, sweat, interstitial fluid, intracellular fluid, hemolysed, lyophilized, or centrifuged blood or any other organic or inorganic materials.

The whole-blood system 200 may comprise a near-patient testing system. As used herein, "near-patient testing system" is used in its ordinary sense and includes, without limitation, test systems that are configured to be used where the patient is rather than exclusively in a laboratory, e.g., systems that can be used at a patient's home, in a clinic, in a hospital, or even in a mobile environment. Users of near-patient testing systems can include patients, family members of patients, clinicians, nurses, or doctors. A "near-patient testing system" could also include a "point-of-care" system.

The whole-blood system 200 may in one embodiment be configured to be operated easily by the patient or user. As such, the system 200 is preferably a portable device. As used herein, "portable" is used in its ordinary sense and means, without limitation, that the system 200 can be easily transported by the patient and used where convenient. For example, the system 200 is advantageously small. In one preferred embodiment, the system 200 is small enough to fit into a purse or backpack. In another embodiment, the system 200 is small enough to fit into a pants pocket. In still another embodiment, the system 200 is small enough to be held in the palm of a hand of the user.

Some of the embodiments described herein employ a sample element to hold a material sample, such as a sample of biological fluid. As used herein, "sample element" is a broad term and is used in its ordinary sense and includes, without limitation, structures that have a sample cell and at least one sample cell wall, but more generally includes any of a number of structures that can hold, support or contain a material sample and that allow electromagnetic radiation to pass through a sample held, supported or contained thereby; e.g., a cuvette, test strip, etc. As used herein, the term "disposable" when applied to a component, such as a sample element, is a broad term and is used in its ordinary sense and means, without limitation, that the component in question is used a finite number of times and then discarded. Some disposable components are used only once and then discarded. Other disposable components are used more than once and then discarded.

The radiation source 220 of the whole-blood system 200 emits electromagnetic radiation in any of a number of spectral ranges, e.g., within infrared wavelengths; in the mid-infrared wavelengths; above about 0.8 $\mu$m; between about 5.0 $\mu$m and about 20.0 $\mu$m; and/or between about 5.25 $\mu$m and about 12.0 $\mu$m. However, in other embodiments the whole-blood system 200 may employ a radiation source 220 which emits in wavelengths found anywhere from the visible spectrum through the microwave spectrum, for example anywhere from about 0.4 $\mu$m to greater than about 100 $\mu$m. In still further embodiments the radiation source emits electromagnetic radiation in wavelengths between about 3.5 $\mu$m and about 14 $\mu$m, or between about 0.8 $\mu$m and about 2.5 $\mu$m, or between about 2.5 $\mu$m and about 20 $\mu$m, or between about 20 $\mu$m and about 100 $\mu$m, or between about 6.85 $\mu$m and about 10.10 $\mu$m.

The radiation emitted from the source 220 is in one embodiment modulated at a frequency between about one-half hertz and about one hundred hertz, in another embodiment between about 2.5 hertz and about 7.5 hertz, in still another embodiment at about 50 hertz, and in yet another embodiment at about 5 hertz. With a modulated radiation source, ambient light sources, such as a flickering fluorescent lamp, can be more easily identified and rejected when analyzing the radiation incident on the detector 250. One source that is suitable for this application is produced by ION OPTICS, INC. and sold under the part number NL5LNC.

The filter 230 permits electromagnetic radiation of selected wavelengths to pass through and impinge upon the cuvette/sample element 240. Preferably, the filter 230 permits radiation at least at about the following wavelengths to pass through to the cuvette/sample element: 3.9, 4.0 $\mu$m, 4.05 $\mu$m, 4.2 $\mu$m, 4.75, 4.95 $\mu$m, 5.25 $\mu$m, 6.12 $\mu$m, 7.4 $\mu$m, 8.0 $\mu$m, 8.45 $\mu$m, 9.25 $\mu$m, 9.5 $\mu$m, 9.65 $\mu$m, 10.4 $\mu$m, 12.2 $\mu$m. In another embodiment, the filter 230 permits radiation at least at about the following wavelengths to pass through to the cuvette/sample element: 5.25 $\mu$m, 6.12 $\mu$m, 6.8 $\mu$m, 8.03 $\mu$m, 8.45 $\mu$m, 9.25 $\mu$m, 9.65 $\mu$m, 10.4 $\mu$m, 12 $\mu$m. In still another embodiment, the filter 230 permits radiation at least at about the following wavelengths to pass through to the cuvette/sample element: 6.85 $\mu$m, 6.97 $\mu$m, 7.39 $\mu$m, 8.23 $\mu$m, 8.62 $\mu$m, 9.02 $\mu$m, 9.22 $\mu$m, 9.43 $\mu$m, 9.62 $\mu$m, and 10.10 $\mu$m. The sets of wavelengths recited above correspond to specific embodiments within the scope of this disclosure. Furthermore, other subsets of the foregoing sets or other combinations of wavelengths can be selected. Finally, other sets of wavelengths can be selected within the scope of this disclosure based on cost of production, development time, availability, and other factors relating to cost, manufacturability, and time to market of the filters used to generate the selected wavelengths, and/or to reduce the total number of filters needed.

In one embodiment, the filter 230 is capable of cycling its passband among a variety of narrow spectral bands or a variety of selected wavelengths. The filter 230 may thus comprise a solid-state tunable infrared filter, such as that available from ION OPTICS INC. The filter 230 could also be implemented as a filter wheel with a plurality of fixed-passband filters mounted on the wheel, generally perpendicular to the direction of the radiation emitted by the source 220. Rotation of the filter wheel alternately presents filters that pass radiation at wavelengths that vary in accordance with the filters as they pass through the field of view of the detector 250.

The detector 250 preferably comprises a 3 mm long by 3 mm wide pyroelectric detector. Suitable examples are produced by DIAS Angewandte Sensorik GmbH of Dresden, Germany, or by BAE Systems (such as its TGS model detector). The detector 250 could alternatively comprise a thermopile, a bolometer, a silicon microbolometer, a lead-salt focal plane array, or a mercury-cadmium-telluride (MCT) detector. Whichever structure is used as the detector 250, it is desirably configured to respond to the radiation incident upon its active surface 254 to produce electrical signals that correspond to the incident radiation.

In one embodiment, the sample element comprises a cuvette 240 which in turn comprises a sample cell 242 configured to hold a sample of tissue and/or fluid (such as whole-blood, blood components, interstitial fluid, intercellular fluid, saliva, urine, sweat and/or other organic or inorganic materials) from a patient within its sample cell. The cuvette 240 is installed in the whole-blood system 200 with the sample cell 242 located at least partially in the optical path 243 between the radiation source 220 and the detector 250. Thus, when radiation is emitted from the source 220 through the filter 230 and the sample cell 242 of the cuvette 240, the detector 250 detects the radiation signal strength at the wavelength(s) of interest. Based on this signal strength, the signal processor 260 determines the degree to which the sample in the cell 242 absorbs radiation at the detected wavelength(s). The concentration of the analyte of interest is then determined from the absorption data via any suitable spectroscopic technique.

As shown in FIG. 13, the whole-blood system 200 can also comprise a sample extractor 280. As used herein, the term "sample extractor" is a broad term and is used in its ordinary sense and refers, without limitation, to or any device which is suitable for drawing a sample of fluid from tissue, such as whole-blood or other bodily fluids through the skin of a patient. In various embodiments, the sample extractor may comprise a lance, laser lance, iontophoretic sampler, gas-jet, fluid-jet or particle-jet perforator, ultrasonic enhancer (used with or without a chemical enhancer), or any other suitable device.

As shown in FIG. 13, the sample extractor 280 could form an opening in an appendage, such as the finger 290, to make whole-blood available to the cuvette 240. It should be understood that other appendages could be used to draw the sample, including but not limited to the forearm. With some embodiments of the sample extractor 280, the user forms a tiny hole or slice through the skin, through which flows a sample of bodily fluid such as whole-blood. Where the sample extractor 280 comprises a lance (see FIG. 14), the sample extractor 280 may comprise a sharp cutting implement made of metal or other rigid materials. One suitable laser lance is the Lasette Plus® produced by Cell Robotics International, Inc. of Albuquerque, N. Mex. If a laser lance, iontophoretic sampler, gas-jet or fluid-jet perforator is used as the sample extractor 280, it could be incorporated into the whole-blood system 200 (see FIG. 13), or it could be a separate device.

Additional information on laser lances can be found in U.S. Pat. No. 5,908,416, issued Jun. 1, 1999, titled LASER DERMAL PERFORATOR; the entirety of this patent is hereby incorporated by reference herein and made a part of this specification. One suitable gas-jet, fluid-jet or particle-jet perforator is disclosed in U.S. Pat. No. 6,207,400, issued Mar. 27, 2001, titled NON- OR MINIMALLY INVASIVE MONITORING METHODS USING PARTICLE DELIVERY METHODS; the entirety of this patent is hereby incorporated by reference herein and made a part of this specification. One suitable iontophoretic sampler is disclosed in U.S. Pat. No. 6,298,254, issued Oct. 2, 2001, titled DEVICE FOR SAMPLING SUBSTANCES USING ALTERNATING POLARITY OF IONTOPHORETIC CURRENT; the entirety of this patent is hereby incorporated by reference herein and made a part of this specification. One suitable ultrasonic enhancer, and chemical enhancers suitable for use therewith, are disclosed in U.S. Pat. No. 5,458,140, titled ENHANCEMENT OF TRANSDERMAL MONITORING APPLICATIONS WITH ULTRASOUND AND CHEMICAL ENHANCERS, issued Oct. 17, 1995, the entire disclosure of which is hereby incorporated by reference and made a part of this specification.

Figure 14:
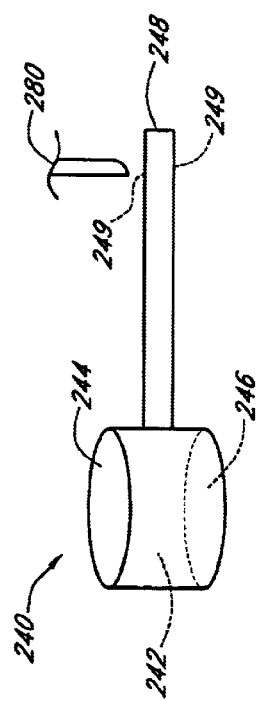
FIG. 14 is a perspective view of one embodiment of a cuvette for use less whole-blood detection system.

FIG. 14 shows one embodiment of a sample element, in the form of a cuvette 240, in greater detail. The cuvette 240 further comprises a sample supply passage 248, a pierceable portion 249, a first window 244, and a second window 246, with the sample cell 242 extending between the windows 244, 246. In one embodiment, the cuvette 240 does not have a second window 246. The first window 244 (or second window 246) is one form of a sample cell wall; in other embodiments of the sample elements and cuvettes disclosed herein, any sample cell wall may be used that at least partially contains, holds or supports a material sample, such as a biological fluid sample, and which is transmissive of at least some bands of electromagnetic radiation, and which may but need not be transmissive of electromagnetic radiation in the visible range. The pierceable portion 249 is an area of the sample supply passage 248 that can be pierced by suitable embodiments of the sample extractor 280. Suitable embodiments of the sample extractor 280 can pierce the portion 249 and the appendage 290 to create a wound in the appendage 290 and to provide an inlet for the blood or other fluid from the wound to enter the cuvette 240. (The sample extractor 280 is shown on the opposite side of the sample element in FIG. 14, as compared to FIG. 13, as it may pierce the portion 249 from either side.)

The windows 244, 246 are preferably optically transmissive in the range of electromagnetic radiation that is emitted by the source 220, or that is permitted to pass through the filter 230. In one embodiment, the material that makes up the windows 244, 246 is completely transmissive, i.e., it does not absorb any of the electromagnetic radiation from the source 220 and filter 230 that is incident upon it. In another embodiment, the material of the windows 244, 246 has some absorption in the electromagnetic range of interest, but its absorption is negligible. In yet another embodiment, the absorption of the material of the windows 244, 246 is not negligible, but it is known and stable for a relatively long period of time. In another embodiment, the absorption of the windows 244, 246 is stable for only a relatively short period of time, but the whole-blood system 200 is configured to observe the absorption of the material and eliminate it from the analyte measurement before the material properties can change measurably.

The windows 244, 246 are made of polypropylene in one embodiment. In another embodiment, the windows 244, 246 are made of polyethylene. Polyethylene and polypropylene are materials having particularly advantageous properties for handling and manufacturing, as is known in the art. Also, polypropylene can be arranged in a number of structures, e.g., isotactic, atactic and syndiotactic, which may enhance the flow characteristics of the sample in the sample element. Preferably the windows 244, 246 are made of durable and easily manufactureable materials, such as the above-mentioned polypropylene or polyethylene, or silicon or any other suitable material. The windows 244, 246 can be made of any suitable polymer, which can be isotactic, atactic or syndiotactic in structure.

The distance between the windows 244, 246 comprises an optical pathlength and can be between about 1 $\mu$m and about 100 $\mu$m. In one embodiment, the optical pathlength is between about 10 $\mu$m and about 40 $\mu$m, or between about 25 $\mu$m and about 60 $\mu$m, or between about 30 $\mu$m and about 50 $\mu$m. In still another embodiment, the optical pathlength is about 25 $\mu$m. The transverse size of each of the windows 244, 246 is preferably about equal to the size of the detector 250. In one embodiment, the windows are round with a diameter of about 3 mm. In this embodiment, where the optical pathlength is about 25 $\mu$m the volume of the sample cell 242 is about 0.177 $\mu$L. In one embodiment, the length of the sample supply passage 248 is about 6 mm, the height of the sample supply passage 248 is about 1 mm, and the thickness of the sample supply passage 248 is about equal to the thickness of the sample cell, e.g., 25 $\mu$m. The volume of the sample supply passage is about 0.150 $\mu$L. Thus, the total volume of the cuvette 240 in one embodiment is about 0.327 $\mu$L. Of course, the volume of the cuvette 240/sample cell 242/etc. can vary, depending on many variables, such as the size and sensitivity of the detectors 250, the intensity of the radiation emitted by the source 220, the expected flow properties of the sample, and whether flow enhancers (discussed below) are incorporated into the cuvette 240. The transport of fluid to the sample cell 242 is achieved preferably through capillary action, but may also be achieved through wicking, or a combination of wicking and capillary action.

Figure 16A:
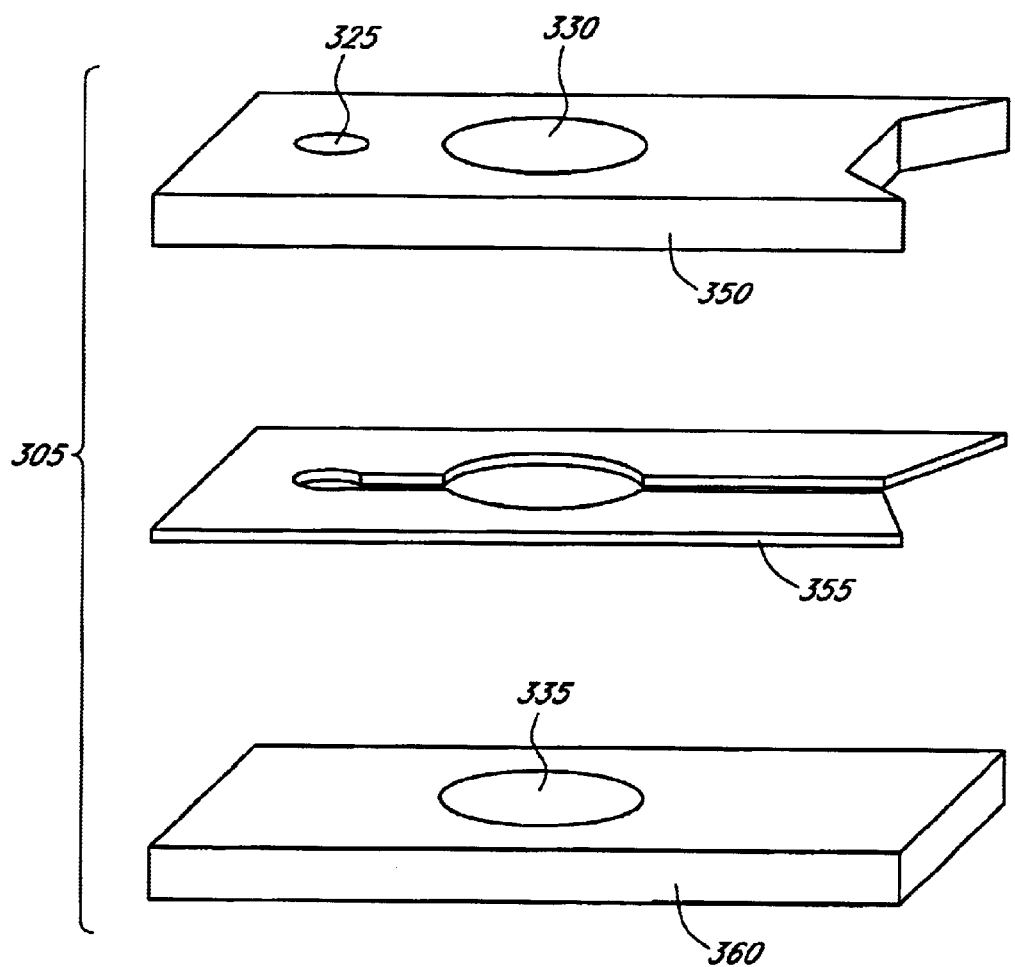
FIG. 16A is an exploded perspective view of the cuvette of FIG. 15.

FIGS. 15–17 depict another embodiment of a cuvette 305 that could be used in connection with the whole-blood system 200. The cuvette 305 comprises a sample cell 310, a sample supply passage 315, an air vent passage 320, and a vent 325. As best seen in FIGS. 16, 16A and 17, the cuvette also comprises a first sample cell window 330 having an inner side 332, and a second sample cell window 335 having an inner side 337. As discussed above, the window(s) 330/335 in some embodiments also comprise sample cell wall(s). The cuvette 305 also comprises an opening 317 at the end of the sample supply passage 315 opposite the sample cell 310. The cuvette 305 is preferably about ¼–⅛ inch wide and about ¾ inch long; however, other dimensions are possible while still achieving the advantages of the cuvette 305.

The sample cell 310 is defined between the inner side 332 of the first sample cell window 330 and the inner side 337 of the second sample cell window 335. The perpendicular distance T between the two inner sides 332, 337 comprises an optical pathlength that can be between about 1 $\mu$m and about 1.22 mm. The optical pathlength can alternatively be between about 1 $\mu$m and about 100 $\mu$m. The optical pathlength could still alternatively be about 80 $\mu$m, but is preferably between about 10 $\mu$m and about 50 $\mu$m. In another embodiment, the optical pathlength is about 25 $\mu$m. The windows 330, 335 are preferably formed from any of the materials discussed above as possessing sufficient radiation transmissivity. The thickness of each window is preferably as small as possible without overly weakening the sample cell 310 or cuvette 305.

Once a wound is made in the appendage 290, the opening 317 of the sample supply passage 315 of the cuvette 305 is placed in contact with the fluid that flows from the wound. In another embodiment, the sample is obtained without creating a wound, e.g. as is done with a saliva sample. In that case, the opening 317 of the sample supply passage 315 of the cuvette 305 is placed in contact with the fluid obtained without creating a wound. The fluid is then transported through the sample supply passage 315 and into the sample cell 310 via capillary action. The air vent passage 320 improves the capillary action by preventing the buildup of air pressure within the cuvette and allowing the blood to displace the air as the blood flows therein.

Other mechanisms may be employed to transport the sample to the sample cell 310. For example, wicking could be used by providing a wicking material in at least a portion of the sample supply passage 315. In another variation, wicking and capillary action could be used together to transport the sample to the sample cell 310. Membranes could also be positioned within the sample supply passage 315 to move the blood while at the same time filtering out components that might complicate the optical measurement performed by the whole-blood system 200.

FIGS. 16 and 16A depict one approach to constructing the cuvette 305. In this approach, the cuvette 305 comprises a first layer 350, a second layer 355, and a third layer 360. The second layer 355 is positioned between the first layer 350 and the third layer 360. The first layer 350 forms the first sample cell window 330 and the vent 325. As mentioned above, the vent 325 provides an escape for the air that is in the sample cell 310. While the vent 325 is shown on the first layer 350, it could also be positioned on the third layer 360, or could be a cutout in the second layer, and would then be located between the first layer 360 and the third layer 360 The third layer 360 forms the second sample cell window 335.

The second layer 355 may be formed entirely of an adhesive that joins the first and third layers 350, 360. In other embodiments, the second layer may be formed from similar materials as the first and third layers, or any other suitable material. The second layer 355 may also be formed as a carrier with an adhesive deposited on both sides thereof. The second layer 355 forms the sample supply passage 315, the air vent passage 320, and the sample cell 310. The thickness of the second layer 355 can be between about 1 $\mu$m and about 1.22 mm. This thickness can alternatively be between about 1 $\mu$m and about 100 $\mu$m. This thickness could alternatively be about 80 $\mu$m, but is preferably between about 10 $\mu$m and about 50 $\mu$m. In another embodiment, the second layer thickness is about 25 $\mu$m.

In other embodiments, the second layer 355 can be constructed as an adhesive film having a cutout portion to define the passages 315, 320, or as a cutout surrounded by adhesive.

Further information can be found in U.S. Patent Application Ser. No. 10/055,875, filed Jan. 22, 2002, titled REAGENT-LESS WHOLE-BLOOD GLUCOSE METER. The entire contents of this patent application are hereby incorporated by reference herein and made a part of this specification.

II. Sample Adapter

A method and device for reducing measurement error in a noninvasive monitor (such as, but not limited to, the noninvasive system 10) when measuring the concentration of an analyte, e.g., glucose, in the tissue of a patient is disclosed. The method involves measuring properties of the analyte in a sample of blood, whole blood or any other suitable body fluid(s) withdrawn from the patient. The method can also involve using the analyte property measurements to reduce patient-specific calibration error of the noninvasive monitor. In another variation, the noninvasive monitor, in combination with an adapter, measures analyte concentration in a sample of blood, whole blood or any other suitable body fluid(s) withdrawn from the patient, i.e., a makes an invasive or "whole blood" measurement. An apparatus for calibrating the noninvasive monitor is also disclosed.

In the remainder of this section and in the drawings related thereto, various methods and devices will be described or depicted in the context of withdrawing, handling, containing, analyzing, etc. samples of blood or whole blood withdrawn from a patient. It should be understood, however, that the methods and devices disclosed herein are not limited to withdrawing, handling, containing, analyzing, etc. blood or whole blood, and that the disclosed methods and devices can be used with any suitable body fluid or sample withdrawn from a patient, such as whole blood, blood component(s), interstitial fluid or intercellular fluid obtained invasively, or saliva or urine obtained noninvasively, or any collection of organic or inorganic material. Therefore any mention of "blood" or "whole blood" should not be construed as limiting the device or method in question use with blood or whole blood.

Monitor calibration error can arise from several sources, including physiological variation across the patient population. Patient-specific monitor calibration error can arise from, for example, the skin condition or the physical condition of the patient. This error can be estimated and corrected by performing an invasive or whole blood measurement of analyte concentration in each patient, comparing the result to a measurement by the noninvasive monitor, and correcting the noninvasive monitor for any observed differences between the two measurements. In one embodiment, the traditional analyte concentration measurement is performed on blood withdrawn from the patient by using, for example, a needle, laser, lancet, finger-stick, or any other suitable sample extractor, including any of those disclosed herein. The traditional or invasive measurement selected is any of a number of highly accurate techniques well known to those skilled in the art. For example, a colorimetric, amperometric or coulombometric technique could be employed. In one embodiment, the invasive measurement is performed with the whole-blood system 200.

Figure 18:
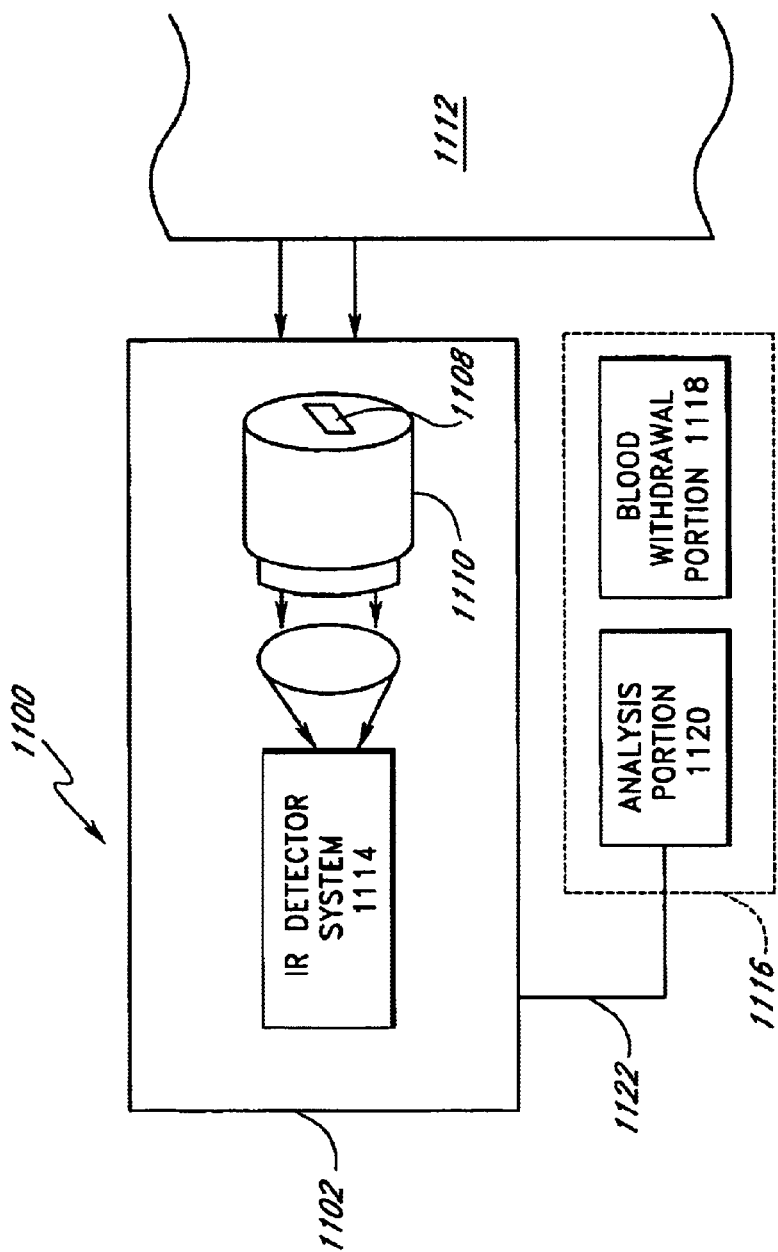
FIG. 18 shows a pictorial representation of a monitor that includes a non-invasive detection unit and a traditional measurement system.

As shown in FIG. 18, the monitor 1100 comprises a noninvasive detection unit 1102 and a traditional measurement system 1116. In the illustrated embodiment, the noninvasive detection unit 1102 comprises an analyzer window 1108, a thermal element 1110 capable of inducing a thermal gradient at the surface of the patient's skin 1112, and an infrared radiation detector system 1114 capable of measuring radiation emitted from the patient's skin or body at wavelengths selected to highlight or isolate the absorptive effects of the analyte of interest, for example, at one or more analyte absorbance wavelength peaks and at one or more reference wavelengths. However, one of skill in the art will appreciate that the noninvasive detection unit 1102 can comprise any instrument, such as but not limited to the noninvasive system 10, which has the capability to determine the concentration of an analyte in in-vivo tissue samples or bodily fluids.

In one embodiment, the traditional measurement system 1116 has a blood-withdrawal portion 1118 and an analysis portion 1120. The traditional measurement system 1116, via the analysis portion 1120, is capable of analyzing whole blood (or other body fluid(s)) withdrawn from the patient with the withdrawal portion 1118 and providing a value or values to the monitor indicating analyte concentration in the blood (or other fluid(s)) withdrawn. Generally, the blood-withdrawal portion 1118 comprises a needle, laser, lancet, finger-stick, etc. (or any other suitable sample extractor, including any of those disclosed herein), and/or any supporting hardware used for holding a withdrawn sample and/or placing the sample on or in the analysis portion 1120. In one embodiment, the whole-blood system 200 comprises at least part of the traditional measurement system 1116.

In one embodiment, shown in FIG. 18, the analysis portion 1120 (in one embodiment, the whole-blood system 200) is a separate unit connected to the noninvasive detection unit 1102 through a data communication line 1122 to facilitate communication of analyte-concentration information to the noninvasive detection unit 1102. The analysis portion 1120 can also be made as an integral component of the monitor 1100. In one preferred variation of the monitor 1100, the analysis portion 1120 of the traditional measurement system 1116 is an electro-chemical monitor. In this embodiment, the monitor 1100 is configured to receive a conventional whole blood electrochemical test strip with blood added thereto. The analysis portion 1120 of the traditional measurement system 1116 can then perform the electro-chemical analyte measurement.

Both the integral construction of the monitor 1100 and the use of the data link 1122 advantageously eliminate human transcription, which would otherwise be a source of human transcription error. Human transcription involves the manual entry, using an input device, such as a dial, keyboard, or other similar manual input device, of a value into a measurement device, such as the monitor 1100. The transcription error avoided by the construction of the monitor 1100 would occur if the user entered a wrong value using the input device. Such errors, which would ordinarily cause all subsequent measurements to be inaccurate, would otherwise be very difficult to eliminate.

Advantageously, at least the blood withdrawal portion 1118 of the device 1116 may be configured as a single use item. In one embodiment, the blood withdrawal portion 1118 of the device 1116 is a single use device, i.e., one configured to be used only once.

Figure 19:
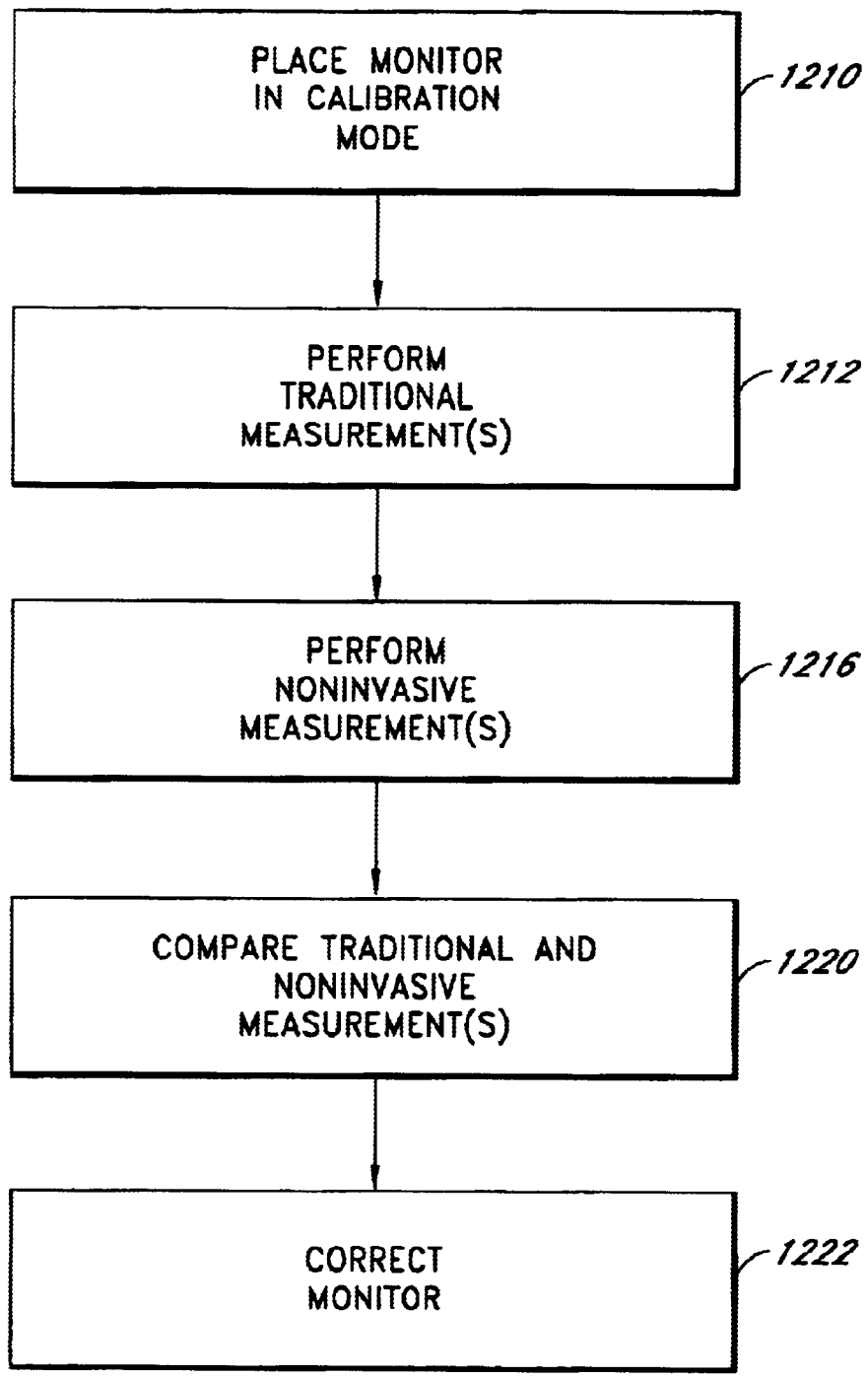
FIG. 19 shows a process flow for calibrating the monitor of FIG. 18.

FIG. 19 is a flow chart of a method of operation of the monitor 1100. In one embodiment of this method, the noninvasive detection unit 1102 comprises a thermal element 1110 capable of inducing a thermal gradient at the surface of the patient's skin 1112, as described above. The method may comprise switching the monitor 1100 to a patient calibration mode in a step 1210. Then in a step 1212, the operator performs a traditional or invasive measurement using the analysis device 11116. This is done by withdrawing a sample of whole blood or any other suitable body fluid(s) from the patient and analyzing the sample in the device 1116 to determine the analyte concentration in the sample. In another embodiment, the step 1212 comprises performing multiple measurements to produce a series of data. These data can be manipulated to yield numerical values relating to the analyte concentration in the sample.

In a step 1216, the operator uses the noninvasive detection unit 1102 to measure the analyte concentration in the patient's blood/tissue. In one embodiment of the method shown in FIG. 19, the step 1216 comprises placing the thermal gradient inducing means of the monitor 1100 in contact with the patient's skin 1112 at a measurement site, inducing a thermal gradient in the patient's skin, and performing an analyte measurement by detecting and analyzing infrared radiation at selected wavelengths. As in the step 1212, another embodiment of the step 1216 comprises performing multiple measurements to produce a series of data representing the analyte concentration. As mentioned above, one of skill in the art will appreciate that the noninvasive detection unit 1102 can comprise any instrument, such as the noninvasive system 10, which has the capability to determine the concentration of an analyte in in-vivo tissue samples or bodily fluids.

Next in a step 1220, the analyte measurements performed in the step 1212 and the step 1216 are compared to estimate the calibration error. Finally, in a step 1222 the measurement output of the monitor is corrected using the calibration error estimated in step 1220 to correct for the patient-specific monitor calibration error.

Figure 20:
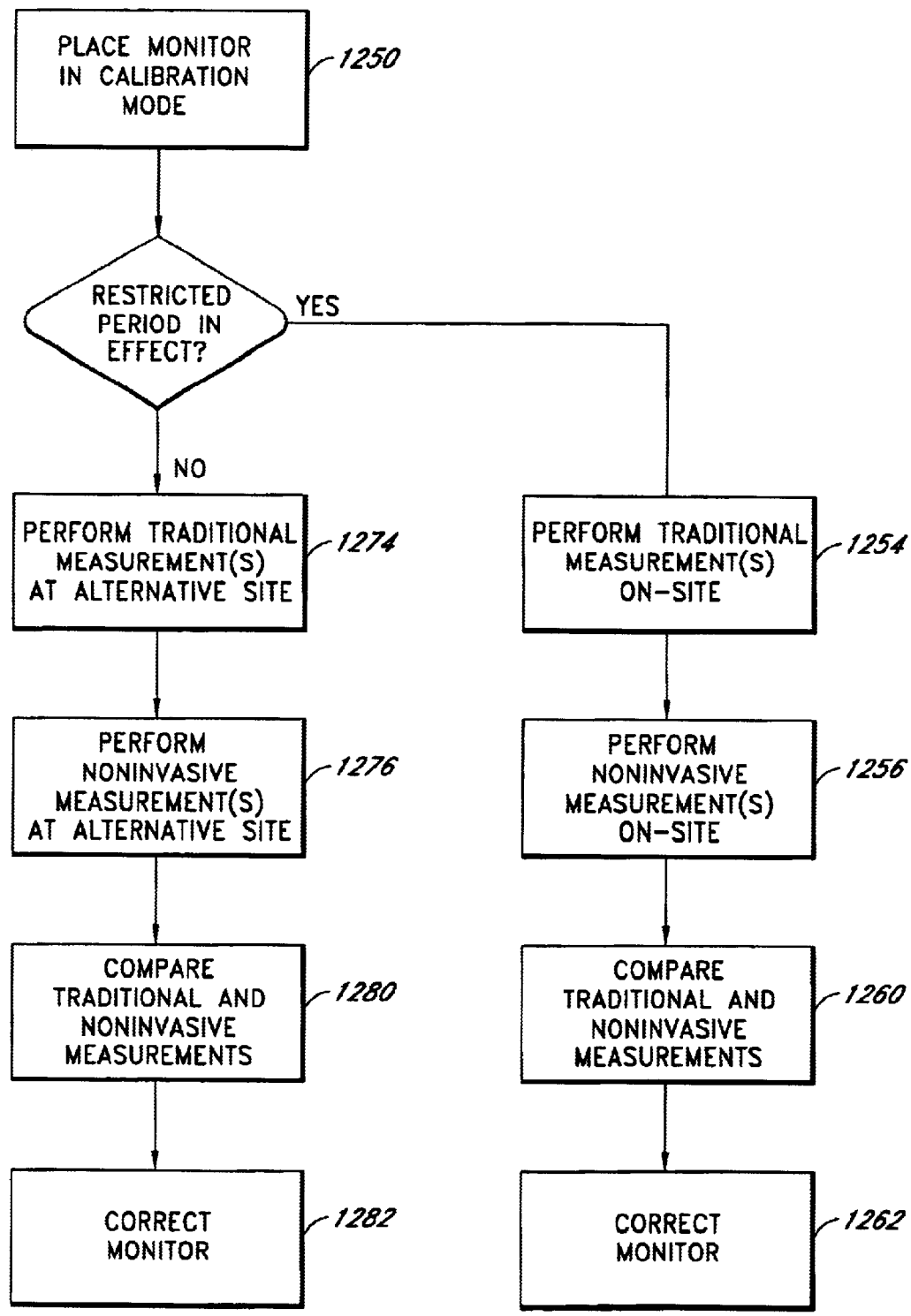
FIG. 20 shows a variation of the process flow of FIG. 19 wherein a restricted period may be applied after the subject eats.

FIG. 20 is a flow chart of another variation of the method of operation of the monitor 1100. This variation addresses where and when measurements are to be taken. More particularly, the method involves the choice of a location on a subject's body at which to take the analyte measurement, preferably based on the amount of time that has elapsed since the last time the subject ate. A restricted period commences after the subject eats. This restricted period is characterized by a restriction on where the subject may take analyte measurements; specifically, the subject is restricted to taking measurements "on-site" (on a finger or fingertip) during a restricted period.

In contrast, when no restricted period is in effect (i.e., the designated time interval has elapsed since the last time the subject ate) the subject may take analyte measurements either on-site or at an alternative site such as, for example, the forearm. It is to be understood, however, that "alternative site" refers to any location other than the on-site positions.

The method shown in FIG. 20 may comprise switching the monitor 1100 to a patient calibration mode in a step 1250. Then in a step 252, the operator determines whether there is a restricted period in effect. In one embodiment, the restricted period lasts from about 0.5 to about 3 hours after the subject eats. In another embodiment, the restricted period lasts from about 1.0 to about 2 hours. In another embodiment, the restricted period lasts from about 1.5 to about 2 hours. In a presently preferred embodiment, the restricted period lasts about 2 hours. If there is a restricted period in effect, then in a step 1254, the operator performs a traditional or invasive measurement on-site using the analysis device 1116. This is done by withdrawing a sample of blood, whole blood or any other suitable body fluid(s) from the patient and analyzing the sample in the device 1116 to determine the analyte concentration in the sample.

Then in a step 1256, the noninvasive detection unit 1102 measures the analyte concentration on-site. The step 1256 may comprise placing the thermal gradient inducing means of the monitor 1100 in contact with the patient's skin 1112 at a measurement site, inducing a thermal gradient in the patient's skin, and performing an analyte measurement by detecting and analyzing thermal radiation at selected wavelengths. As mentioned above, however, one of skill in the art will appreciate that the noninvasive detection unit 1102 can comprise any instrument, such as the noninvasive system 10, which has the capability to determine the concentration of an analyte in in-vivo tissue samples or bodily fluids.

Next in a step 1260, the analyte measurements performed in the step 1254 and the step 1256 are compared to estimate the calibration error. Finally, in a step 1262 the measurement output of the monitor is corrected using the calibration error estimated in step 1260 to correct for the patient-specific monitor calibration error.

If no restricted period in effect, then in a step 1274, the operator performs a traditional or invasive measurement at an alternative site measurement location using the analysis device 1116. As mentioned above, the traditional or invasive measurement at the alternative site measurement location is done by withdrawing a blood sample from the patient and analyzing the blood sample in the device 1116 to determine the analyte concentration of the blood sample.

In a step 1276, the noninvasive detection unit 1102 measures, at an alternative site measurement location, the analyte concentration of the blood. As above, the step 1276 may comprise placing the thermal gradient inducing means of the monitor 1100 in contact with the patient's skin 1112 at a measurement site, inducing a thermal gradient in the patient's skin, and performing an analyte measurement by detecting and analyzing thermal radiation at selected wavelengths. Again, the noninvasive detection unit 1102 can comprise any instrument, such as the noninvasive system 10, which has the capability to determine the concentration of an analyte in in-vivo tissue samples or bodily fluids.

Next in a step 1280, the analyte measurements performed in the step 1274 and the step 1276 are compared to estimate the calibration error. Finally, in a step 1282 the measurement output of the monitor is corrected using the calibration error estimated in step 1280 to correct for the observed patient-specific monitor calibration error.

In any of the methods described herein, calibration can also be performed by using the noninvasive monitor to analyze analyte concentration in withdrawn blood. In this embodiment, the analysis portion 1120 of the analysis device 1116 could be omitted. Instead, the monitor 1100 performs the analyte concentration measurement on a blood sample withdrawn from the patient, i.e., whole blood analysis. This process is described in more detail below in connection with FIGS. 29 and 30.

Figure 21:
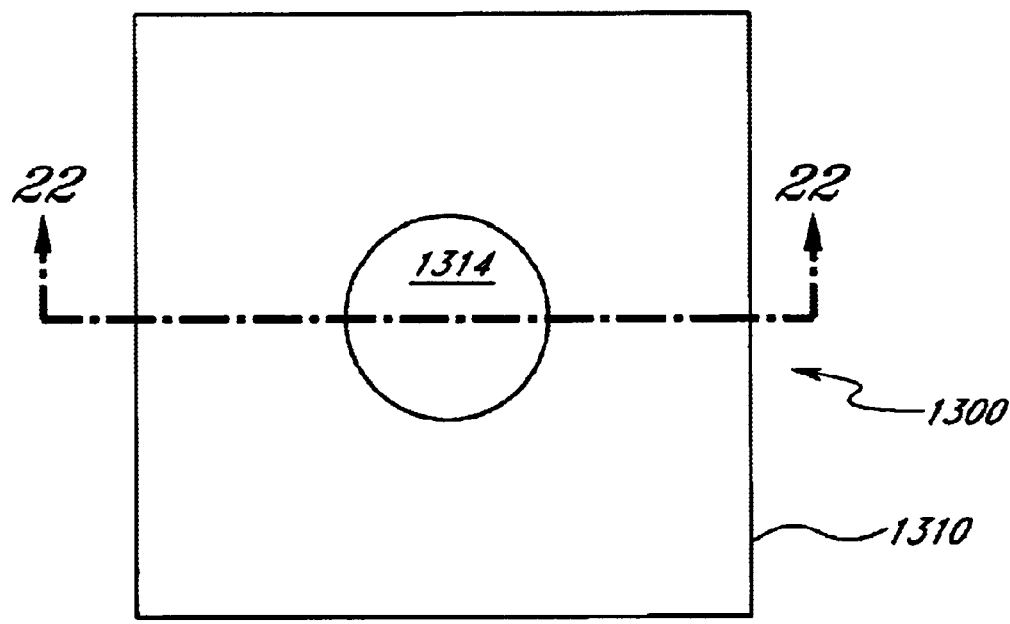
FIG. 21 shows a top view of a whole blood adapter.
Figure 22:
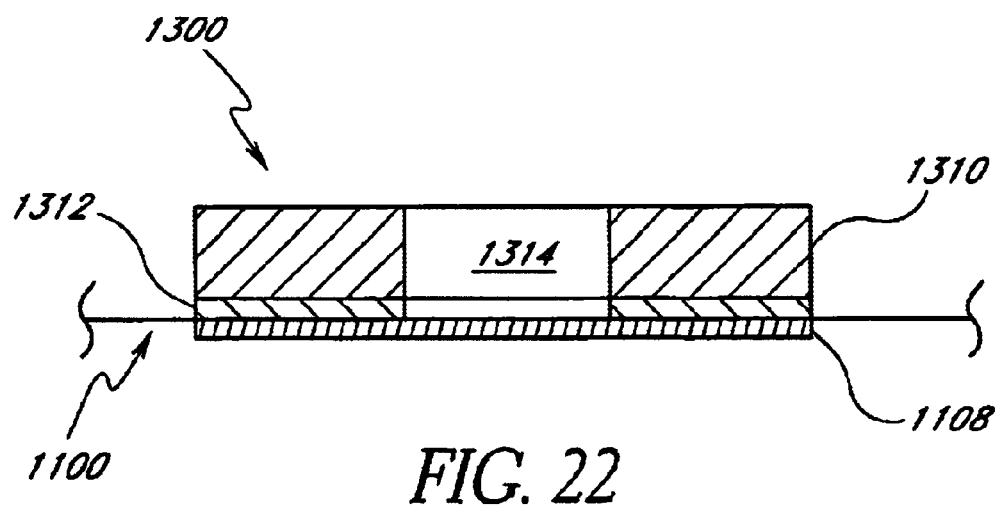
FIG. 22 shows a cross-sectional view of the whole blood adapter of FIG. 21.

FIGS. 21 and 22 depict one embodiment of an adapter 1300 which can be used to facilitate analysis of samples of body fluids (such as blood, whole blood or any other suitable body fluid(s) withdrawn from a patient) by any noninvasive monitor (such as but not limited to the noninvasive system 10) having a window, lens, or other opening for passing or receiving energy to or from a sample or living tissue. In one embodiment the adapter 1300 comprises a base material 1310. The material 1310 is preferably a hydrophobic material, e.g., Kapton. The adapter 1300 is configured to be applied to the analyzer window 1108 of the monitor 1100 and sized to cover a large portion of the window 1108. The adapter 1300 also has a sample accommodating volume 1314 configured to receive a small sample of blood, whole blood or other body fluid(s) that extends between openings positioned on opposite sides of the base material 1310. In one embodiment, the sample accommodating volume 1314 is about 250 microliters.

In another embodiment, the adapter 1300 also comprises an adhesive backing 1312. The adhesive backing 1312 is selected from materials that do not give any analyte absorption signature, i.e., those materials that do not emit thermal radiation in the same spectra as the analyte. This has the effect of "passivating" the portions of the window covered by the adhesive 1312. In still another embodiment, an anti-clotting agent (such as heparin) is added to a blood sample before placement in the adapter.

In still another embodiment, the control software and/or electronics of the noninvasive unit 1102 is configured to account for any observed rate of consumption of the analyte in the sample after placement of the sample in the adapter 1300. For example, the software/electronics may accept input of an observed consumption rate and use a time measurement (taken from any of (i) elapsed time since placement of the adapter on the window, (ii) elapsed time since initiation of an analyte-concentration measurement; or (iii) elapsed time since sample withdrawal) to calculate a consumption adjustment. The software/electronics may then adjust its initial measurement of analyte concentration by the consumption adjustment, to arrive at a consumption-adjusted analyte concentration measurement. In another embodiment, the software/electronics assumes a consumption rate based on input of the sample type and analyte(s) measured. For example, if the user desires to measure the concentration of glucose in whole blood, upon input of the analyte and sample type, a consumption rate of about 0.16 mg/dL/min could be assumed and employed in calculation of the consumption adjustment.

In operation, the adapter 1300 is applied to the analyzer window 1108. Then a drop of the withdrawn sample is placed in the sample accommodating volume 1314. Once the sample is applied to the sample accommodating volume 1314, the analyte concentration in the sample is measured in the usual manner. After the monitor 1100 performs the measurement, the adapter 1300 is removed from the window 1108 of the monitor 1100, and any of the sample left on the window is removed. In one embodiment, the adapter 1300, with the sample placed therein, is shaken before placement on the window 1008; it is believed that shaking counteracts any settlement and separation of the components of the sample, thereby promoting increased measurement accuracy. This can be done using a sterilizing solution, such as isopropyl alcohol or other well known sterilizing solutions.

Figure 23:
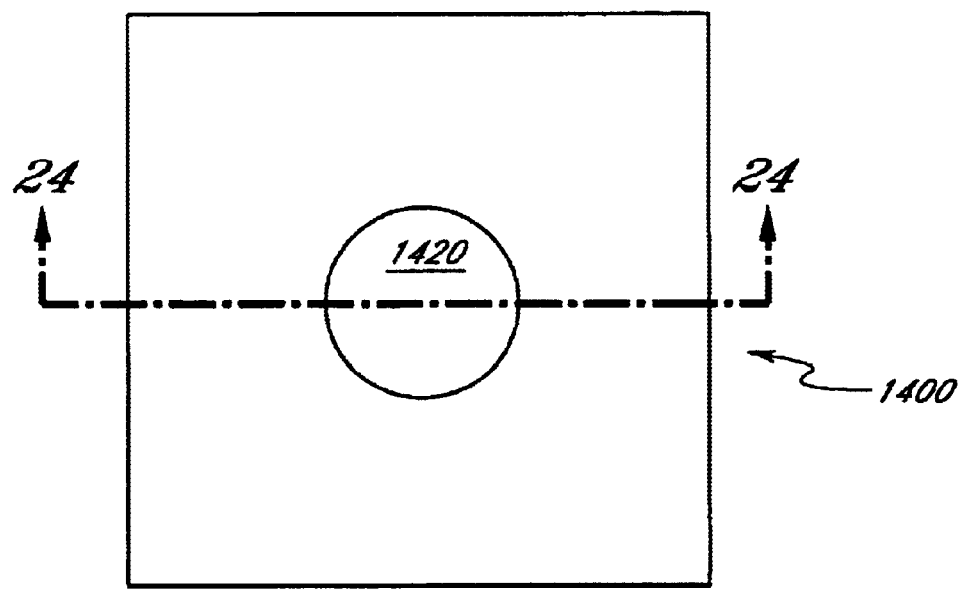
FIG. 23 shows a top view of a variation of the whole blood adapter.
Figure 24:
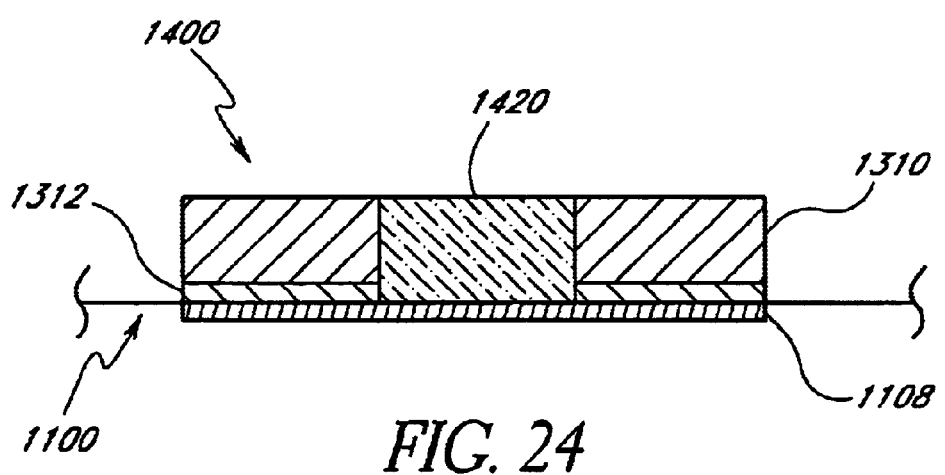
FIG. 24 shows a cross-sectional view of the whole blood adapter of FIG. 23.

In one variation shown in FIGS. 23 and 24, an adapter 1400 similar to the adapter 1300 has a wicking medium 1420 that captures the sample using capillary forces. Capillary forces cause the sample to be drawn into the wicking medium. In operation, after the adapter 1400 is removed from the window 1108 of the monitor 1100, the sample remains captured in the wicking material 1420. This reduces the amount of the sample remaining on the window 1108 after the adapter 1400 is removed. Thus, a simple wipe with an alcohol soaked pad is sufficient to clean the window.

Figure 25:
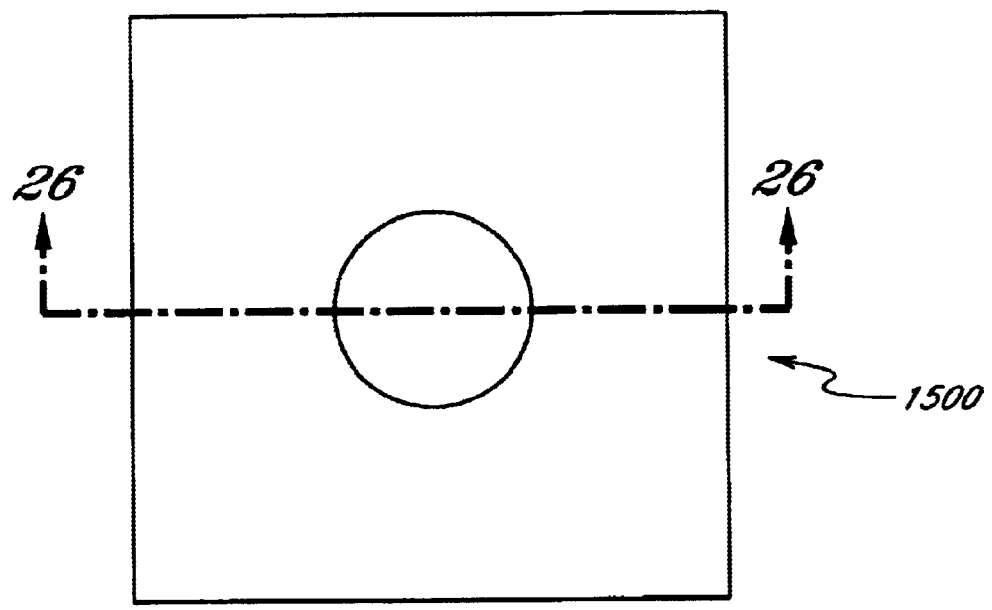
FIG. 25 shows a top view of another variation of the whole blood adapter.
Figure 26:
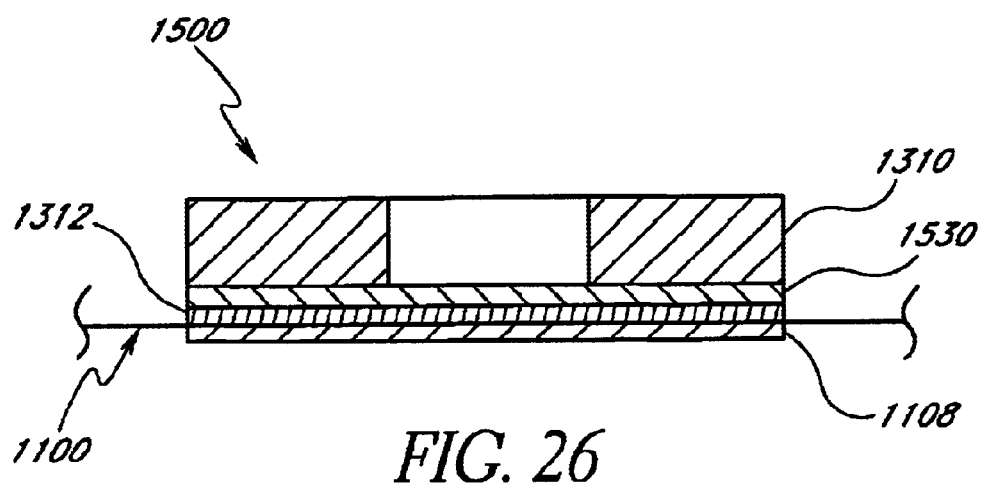
FIG. 26 shows a cross-sectional view of the whole blood adapter of FIG. 25.
Figure 27:
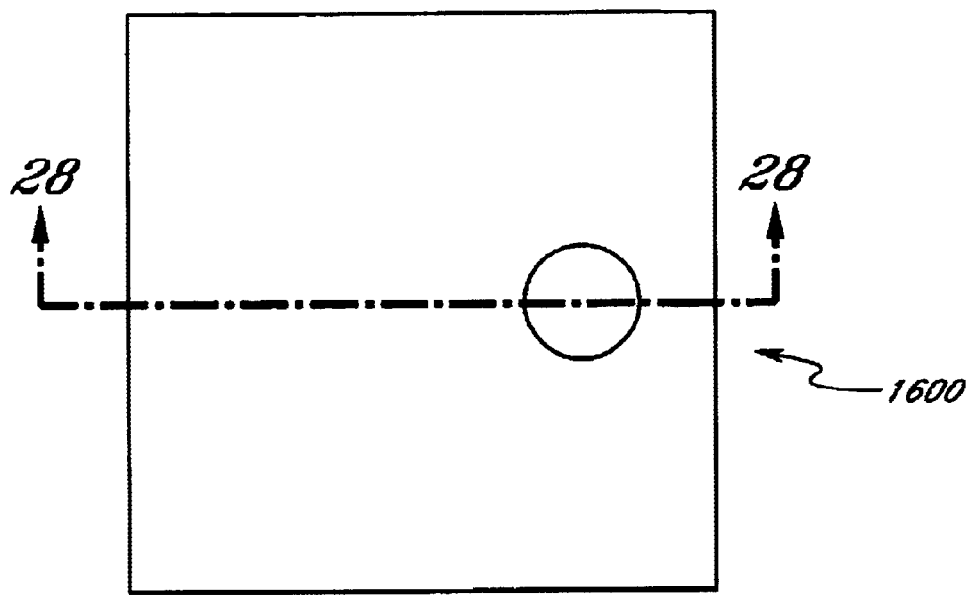
FIG. 27 shows a top view of another variation of the whole blood adapter.
Figure 28:
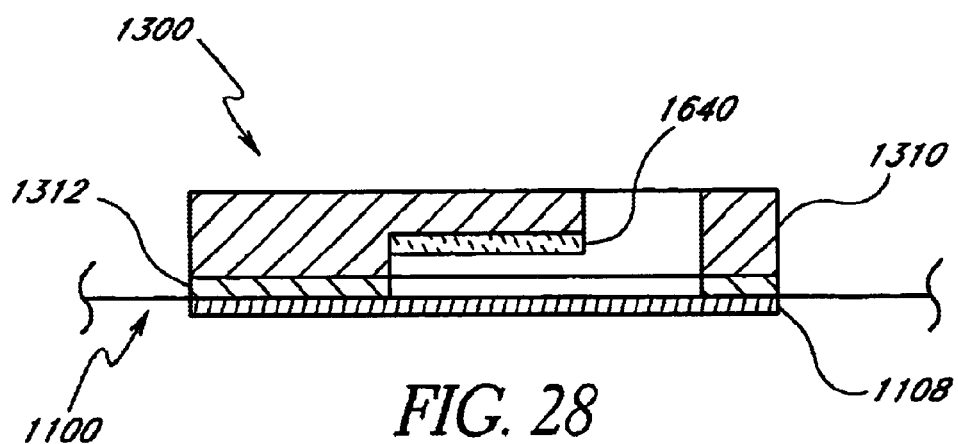
FIG. 28 shows a cross-sectional view of the whole blood adapter of FIG. 27.

In another embodiment shown in FIGS. 25 and 26, an adapter 1500 comprises a thin optically transparent material layer 1530 to prevent the sample from coming into contact with the analyzer window 1108. Suitable materials for the layer 1530 include mylar, vinyl, and polypropylene. After the measurement is made the adapter 1500, including the thin layer 1530, is removed and discarded. There is no need to clean the window 1108 as the sample did not contact the window. In the embodiments illustrated in FIGS. 21–26, a column of the sample fluid(s) is captured in the sample accommodating volume having an outer diameter approximately equal to the diameter of the opening in the base material and a height approximately equal to the thickness of the base material. The amount of the sample required is limited by the diameter of the opening in the base material.

In yet another embodiment shown in FIG. 6, an adapter 1600 is configured to further limit the minimum amount of the sample by further reducing the height of the sample column and by reducing the diameter of the opening in the base material. As a result, the sample accommodating volume is reduced. Under normal operating conditions the noninvasive monitor disclosed in U.S. Pat. No. 6,198,949 will sense an analyte to a depth of several hundred microns in the sample under analysis. If the height of the sample is reduced, the measurement will be made on only the available height. Such a measurement can be performed by incorporating a neutral absorption material 1640 such as polyethylene or silicon into the adapter 1600. The material 1640 is positioned in the adapter 1600 so that when the sample is within the adapter 1600 and when the adapter is positioned on the window 1108, the sample is between the material 1640 and the window 1108. The material 1640 must not absorb infrared energy in the wavelength ranges absorbed by the analyte, the sample, or the normal body tissues.

Figure 29:
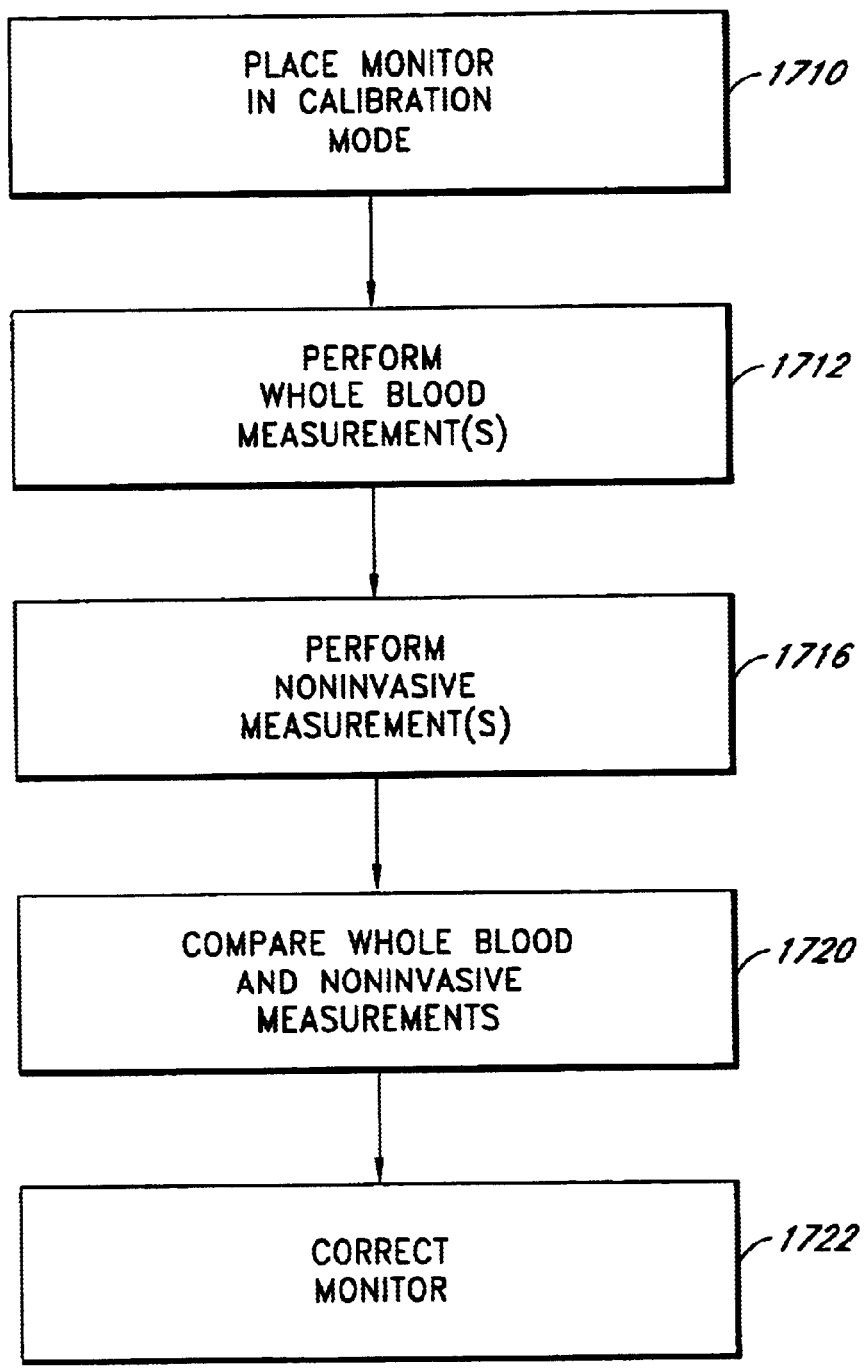
FIG. 29 shows a process flow for calibrating the noninvasive detection unit of FIG. 1.

FIG. 29 is a flow chart of a method of operation of the noninvasive detection unit 1102 of the monitor 1100. (As mentioned above, the noninvasive detection unit 1102 may, but need not, comprise the noninvasive system 10.) In one embodiment of this method, the noninvasive detection unit 1102 comprises a thermal element 1110 capable of inducing a thermal gradient at the surface of the patient's skin 1112, as described above. The method may comprise switching the monitor 1100 to a patient calibration mode in a step 1710. Then in a step 1712, the operator performs with the noninvasive detection unit 1102 an analysis of a sample of body fluid(s) withdrawn from a patient. This is done by withdrawing the sample from the patient and positioning the sample over the analyzer window 1108. The sample may be positioned over the window 1108 by placing the sample in an adapter (e.g., adapter 1300, adapter 1400, adapter 1500, or adapter 1600) and positioning the adapter on the window 1108. In another embodiment, the step 1712 comprises performing multiple measurements to produce a series of data. The data obtained from analysis of the sample can be manipulated to yield numerical values, or an invasive-measurement output, relating to the concentration of the analyte of interest.

In a step 1716, the operator performs noninvasive measurements with the noninvasive detection unit 1102 to measure the analyte concentration within the patient's blood/tissue. In one embodiment of the method shown in FIG. 29, the step 1716 comprises placing the thermal gradient element 1110 of the noninvasive detection unit 1102 in contact with the patient's skin 1112 at a measurement site, inducing a thermal gradient in the patient's skin, and performing an analyte measurement by detecting and analyzing thermal radiation at selected wavelengths. As in the step 1712, another embodiment of the step 1716 comprises performing multiple measurements to produce a series of data representing the analyte concentration. The obtained from the noninvasive measurement(s) then become a noninvasive-measurement output. As mentioned above, the noninvasive detection Unit 1102 can comprise any instrument which has the capability to determine the concentration of an analyte in in-vivo tissue samples or bodily fluids.

Next in a step 1720, the invasive-measurement output generated in the step 1712 and the noninvasive-measurement output generated in the step 1716 are compared to estimate the calibration error. Finally, in a step 1722 the measurement output of the monitor 1100 is corrected using the calibration error estimated in step 1720 to correct for the patient-specific monitor calibration error.

Figure 30:
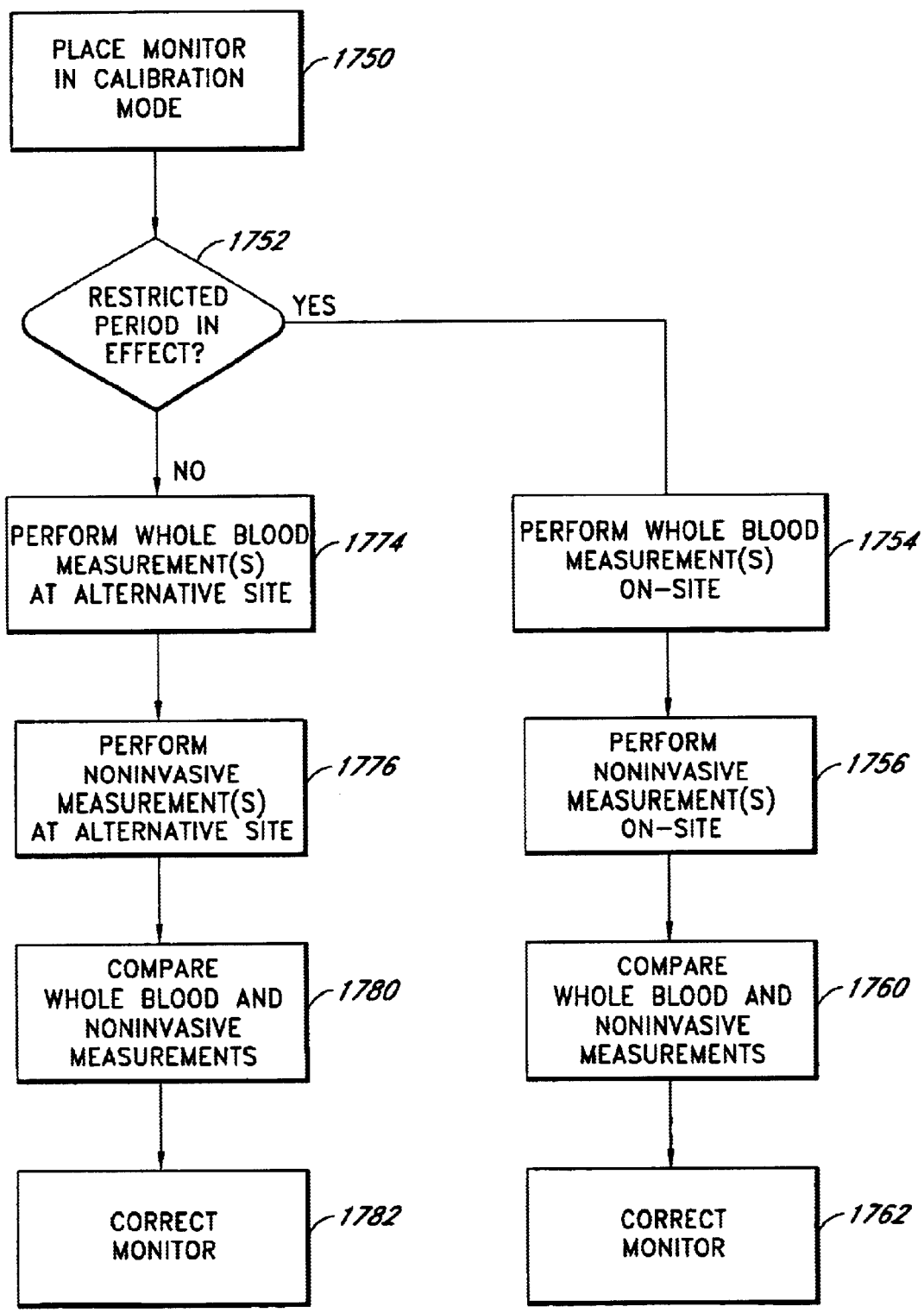
FIG. 30 shows a variation of the process flow of FIG. 29 wherein a restricted period may be applied after the subject eats.

FIG. 30 is a flow chart of another variation of the method of operation of the monitor 1100. This variation addresses where and when measurements are to be taken. More particularly, the method involves the choice of a location on a subject's body at which to take the analyte measurement, preferably based on the amount of time that has elapsed since the last time the subject ate. A restricted period commences after the subject eats. This restricted period is characterized by a restriction on where the subject may take analyte measurements; specifically, the subject is restricted to taking measurements at an on-site location during a restricted period.

In contrast, when no restricted period is in effect (i.e., the designated time interval has elapsed since the last time the subject ate) the subject may take analyte measurements either on-site or at an alternative site measurement location such as, for example, the forearm. It is to be understood, however, that "alternative site" refers to any location other than the on-site positions.

The method shown in FIG. 30 may comprise switching the noninvasive detection unit 1102 to a patient calibration mode in a step 1750. Then in a step 1752, the operator determines whether there is a restricted period in effect. In one embodiment, the restricted period lasts from about 0.5 to about 3 hours after the subject eats. In another embodiment, the restricted period lasts from about 1.0 to about 2 hours. In another embodiment, the restricted period lasts from about 1.5 to about 2 hours. In a presently preferred embodiment, the restricted period lasts about 2 hours. If there is a restricted period in effect, then in a step 1754, the operator performs an invasive or whole blood measurement "on-site" using the noninvasive detection unit 1102. This is done by withdrawing a sample from the patient, placing the sample in an adapter (e.g., adapter 1300, adapter 1400, adapter 1500, or adapter 1600) and analyzing the blood sample in the noninvasive detection unit 1102 to determine the analyte concentration in the sample.

In a step 1756, the operator uses the noninvasive detection unit 1102 to measure analyte concentration on-site. The step 1756 may comprise placing the thermal gradient inducing means of the monitor 1100 in contact with the patient's skin 1112 at an onsite measurement location, inducing a thermal gradient in the patient's skin, and performing an analyte measurement by detecting and analyzing thermal radiation at selected wavelengths. As mentioned above, however, one of skill in the art will appreciate that the noninvasive detection unit 1102 can comprise any instrument, such as the noninvasive system 10, which has the capability to determine the concentration of an analyte in in-vivo tissue samples or bodily fluids.

Next in a step 1760, the analyte measurements performed in the step 1754 and the step 1756 are compared to estimate the calibration error. Finally, in a step 1762 the measurement output of the monitor 1100 is corrected using the calibration error estimated in step 1760 to correct for the patient-specific monitor calibration error.

If no restricted period in effect, then in a step 1774, the operator performs an invasive or whole blood measurement at an alternative site using the noninvasive detection unit 1102. As mentioned above, the invasive or whole blood measurement at the alternative site measurement location is done by withdrawing a sample from the patient, placing the withdrawn sample in an adapter (e.g., adapter 1300, adapter 1400, adapter 1500, or adapter 1600), and analyzing the sample with the noninvasive detection unit 1102 to determine the concentration of the analyte of interest in the withdrawn sample.

In a step 1776, the noninvasive detection unit 1102 measures at an alternative site the analyte concentration in the patient's blood/tissue. As above, the step 1776 may comprise placing the thermal gradient inducing means of the monitor 1100 in contact with the patient's skin 1112 at an alternative site, inducing a thermal gradient in the patient's skin, and performing an analyte measurement by detecting and analyzing thermal radiation at selected wavelengths. In another variation, the analyte measurement of the step 1776 may be performed on-site. As above, the noninvasive detection unit 1102 can comprise any instrument, such as the noninvasive system 10, which has the capability to determine the concentration of an analyte in in-vivo tissue samples or bodily fluids.

Next in a step 1780, the analyte measurements performed in the step 1774 and the step 1776 are compared to estimate the calibration error. Finally, in a step 1782 the measurement output of the monitor is corrected using the calibration error estimated in step 1780 to correct for the observed monitor error.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof Thus, it is intended that the scope of the present invention herein disclosed should not be limited by the particular disclosed embodiments described above, but should be determined only by a fair reading of the claims that follow.

What is claimed is:

1. A method for calibrating a noninvasive detection unit including a window, the method comprising:
    determining whether there is a restricted period in effect;
    selecting an on-site or an alternative site measurement location based on whether a restricted period is in effect;
    withdrawing a sample of bodily fluid from a patient at the selected measurement location, the sample comprising at least one analyte;
    positioning the sample over the window;
    analyzing the analyte in the sample using the noninvasive detection unit and generating an invasive-measurement output representing a characteristic of the analyte;
    placing the window of the noninvasive detection unit in contact with the skin of the patient;
    analyzing the analyte in the tissue of the patient with the noninvasive detection unit;
    generating a noninvasive-measurement output representing the characteristic of the analyte;
    comparing the invasive-measurement output and the noninvasive-measurement output to estimate an error; and
    correcting the noninvasive-measurement output based on said error.

2. The method of claim 1, wherein placing the window of the noninvasive detection unit in contact with the skin of the patient comprises placing the window in contact with the skin of the patient at the on-site measurement location or at the alternative site measurement location based on whether a restricted period is in effect.

3. The method of claim 1, wherein placing the window of the noninvasive detection unit in contact with the skin of the patient further comprises placing a thermal gradient inducing element of said noninvasive detection unit in contact with the skin of the patient.

4. The method of claim 1, further comprising correcting subsequent noninvasive outputs based on said error.

5. The method of claim 1, wherein generating an invasive-measurement output representing a characteristic of the analyte comprises generating an invasive-measurement output representing the concentration of glucose in blood.

6. The method of claim 1, wherein determining whether there is a restricted period in effect comprises measuring an amount of time since a subject has eaten.

7. The method of claim 6, wherein the amount of time measured is from about 0.5 hour to about 3 hours.

8. The method of claim 6, wherein the amount of time measured is from about 1 hours to about 2 hours.

9. The method of claim 6, wherein the amount of time measured is from about 1.5 hours to about 2 hours.

10. The method of claim 6, wherein the amount of time measured is about 2 hours.

* * * * *